United States Patent [19]

Madras et al.

[11] Patent Number: 5,770,180

[45] Date of Patent: Jun. 23, 1998

[54] BRIDGE-SUBSTITUTED TROPANES FOR METHODS OF IMAGING AND THERAPY

[75] Inventors: Bertha K. Madras, Newton; Peter Meltzer, Lexington, both of Mass.

[73] Assignees: Organix, Inc., Woburn; President and Fellows of Harvard College, Cambridge, both of Mass.

[21] Appl. No.: 649,258

[22] Filed: Apr. 26, 1996

Related U.S. Application Data

[60] Continuation-in-part of Ser. No. 548,271, Oct. 25, 1995, abandoned, which is a division of Ser. No. 111,141, Aug. 24, 1993, Pat. No. 5,506,359, which is a continuation-in-part of Ser. No. 934,362, Aug. 24, 1992, abandoned.

[51] Int. Cl.$^6$ ........................ A61K 51/04; C07D 313/00; C07D 451/02

[52] U.S. Cl. ........................ 424/1.81; 424/1.85; 424/1.65; 549/346; 549/350; 549/9; 546/124; 546/127; 546/130

[58] Field of Search ................................. 424/1.81, 1.85, 424/1.65; 549/346, 350, 9; 546/127, 130, 124; 514/304

[56] References Cited

U.S. PATENT DOCUMENTS

| | | | |
|---|---|---|---|
| 3,040,049 | 6/1962 | Harms | 260/292 |
| 3,351,625 | 11/1967 | Harms | 260/292 |
| 3,452,029 | 6/1969 | Childress et al. . | |
| 3,813,404 | 5/1974 | Clarke et al. . | |
| 4,393,069 | 7/1983 | Langbein et al. . | |
| 5,128,118 | 7/1992 | Carroll et al. . | |

OTHER PUBLICATIONS

Balster et al. "Potent Substituted-3β-phenyltropane Analogs of Cocaine have Cocaine-like Discriminative Stimulus Effects" Drug and Alcohol Dependence, 29:145–151 (1991) Without Month.

Boja et al. "Isothiocyanate Derivatives of Cocaine: Irreversible Inhibition of Ligand Binding at the Dopamine Transporter" Molecular Pharmacology, 39:339–345 (1991) Without Month.

Boja et al. "New, Potent Cocaine Analogs: Ligand Binding and Transport Studies in Rat Striatum" European J. of Pharmacology, 184:329–332 (1990) Without Month.

Brownell et al. "Glucose Utilization and N-[C-11]-Methyl-2 Carbomethoxy-3-Phenyl Tropane ([C-11]PT) Studies of the Primate Model of Huntington's Disease" J. Nuclear Med. Abs., 32:981 (1991) Without Month.

Canfield et al. "Autoradiographic Localization of Cocaine Binding Sites by [$^3$H]CFT ([$^3$H]WIN 35,428) in the Monkey Brain" Synapse, 6:189–195 (1990) Without Month.

Carroll et al. "Probes for the Cocaine Receptor. Potentially Irreversible Ligands for the Dopamine Transporter" J. Med. Chem., 35:1813–1817 (1992) Without Month.

Carroll et al. "Cocaine Receptor: Biochemical Characterization and Structure–Activity Relationships of Cocaine Analogues at the Dopamine Transporter" J. Med. Chem., 35:969–981 (1992) Without Month.

Carroll et al. "Synthesis, Ligand Binding, QSAR, and CoMFA Study of 3β-(p-Substituted phenyl)tropane-2β-carboxylic Acid Methyl Esters" J. Med. Chem., 34:2719–2725 (1991) Without Month.

Carroll et al. "Synthesis and Ligand Binding of Cocaine Isomers at the Cocaine Receptor" J. Med. Chem., 34:883–886 (1991) Without Month.

Chen et al. "In Vivo Binding, Internalization, and Dopamine-Releasing Effects of [H–3]–CFT (WIN 35,428): A Potential Brain Imaging Ligand for Dopamine Transporter or Cocaine . . . " Soc. Neuro. Abs., 16:309.5 (1990) Without Month.

Clarke et at. "(2–exo–3–endo)–2–Aryltropane–3–carboxylic Esters, a New Class of Narcotic Antagonists" J. Med. Chem., 21:1235–1242 (1978) Without Month.

Clarke et al. "Compounds Affecting the Central Nervous System. 4. 3β–Phenyltropane–2–carboxylic Esters and Analogs" J. Med. Chem., 16:1260–1267 (1973) Without Month.

Cline et al. "Behavior Effects of Novel Cocaine Analogs: A Comparison with in Vivo Receptor Binding Potency" J. Pharm. & Exp. Therapeutics, 260:1174–1179 (1992) Without Month.

Daum et al. "Compounds Affecting the Central Nervous System. 3.$^1$ 3β–Phenyltropan–2–ols" J. Med. Chem., 16:667–670 (1973) Without Month.

Elmaleh et al. "N–[C–11]–Methyl–2B–Carbomethoxy–3B–Phenyl Tropane [C–11]PT) and Glucose Utilization in a Primate Model of Huntington's Disease" J. Nuclear Med. Abs., 32:552 (1991) Without Month.

Elmaleh et al. "Preparation and In Vivo Imaging of N–[C–11]–Methyl–2–Carbomethoxy–3–Phenyl Tropane ([C–11]PT) PT) in Monkey Brain" J. Nuclear Med. Abs., 32:1009 (1991) Without Month.

Elmaleh et al. "PET Imaging Probes for the Cocaine Receptors: A Validation Study in a Nonhuman Primate Model" J. Nuclear Med. Abs., 33:946 (1992) Without Month.

Goodman et al. "Radioiodinated 2β–Carbomethoxy–3β–(4–Chlorophenyl)–8–(3E–and 3Z–Iodopropen–2–YL)Nortropanes: Synthesis of Potential Radioligands for Mapping Cocaine Receptor . . . " J. Nuclear Med. Abs., 33:890 (1992) Without Month.

Hantraye et al. "Dopamine Fiber Detection by [$^{11}$C]–CFT and PET in a Primate Model of Parkinsonism" Clin. Neurosci. and Neuropath., 3:265–268 (1992) Without Month.

Hillier "WIN–35,428" Drugs of the Future, 5:459–460 (1980) Without Month.

(List continued on next page.)

*Primary Examiner*—Gary E. Hollinden
*Assistant Examiner*—Michael G. Hartley
*Attorney, Agent, or Firm*—Fish & Richardson P.C.

[57] ABSTRACT

Disclosed are bridge-substituted analogs of tropanes and benztropines as well as methods for: imaging of cocaine receptors; treatment of cocaine abuse; and imaging and treatment of Parkinson's disease.

15 Claims, 13 Drawing Sheets

OTHER PUBLICATIONS

Horn "Dopamine Uptake: A Review of Progress in the Last Decade" Progress in Neurobiology, 34:387–400 (1990) Without Month.

Innis et al. "Single Photon Emission Computed Tomography Imaging of Monoamine Reuptake Sites in Primate Brain with [$^{123}$I]CIT" Eur. J. of Pharmacol., 200:369–370 (1991) Without Month.

Kaufman et al. "Severe Depletion of Cocaine Recognition Sites Associated With the Dopamine Transporter in Parkinson's–Diseased Striatum" Synapse, 9:43–49 (1991) Without Month.

Kitayama et al. "Dopamine Transporter Site–Directed Mutations Differentially Alter Substrate Transport and Cocaine Binding" Proc. Natl. Acad. Sci., 89:7782–7785 (1992) Without Month.

Kline, Jr. et al. "Synthesis of 3–Arlecgonine Analogues as Inhibitors of Cocaine Binding and Dopamine Uptake" J. Med. Chem., 33:2024–2027 (1990) Without Month.

Leete "2–Carbomethoxy–3–tropinone: An Advanced Intermediate in the Biosynthesis of Cocaine" J. Amer. Chem. Soc., 105:6727–6728 (1983) Without Month.

Madras "$^{11}$C–WIN 35,428 for Detecting Dopamine Depletion in Mild Parkinson's Disease" Annals of Neuro., 35:376–377 (1994) Without Month.

Madras et at. "N–Modified Fluorophenyltropane Analogs of Cocaine With High Affinity for Cocaine Receptors" Pharmacol. Biochem. & Behav., 35:949–953 (1990) Without Month.

Madras et al. "[$^3$H]CFT: A Novel High Affinity Ligand for Cocaine Receptors" Soc. for Neurosci. Abstracts, 15:803 (1989) Without Month.

Madras et al. "Cocaine Receptors Labeled by [3H] 2β–Carbomethoxy–3β–(4–fluorophenyl)tropane" Molecular Pharmacology, 36:518–524 (1989) Without Month.

Madras et al. "[3H](–)–Cocaine Binding to Membranes of Monkey Striatum" FASEB J. Abstracts, 2:A1137 (1988) Without Month.

Meltzer et al. "Substituted 3–Phenyltropane Analogs of Cocaine: Synthesis, Inhibition of Binding at Cocaine Recognition Sites, and Positron Emission Tomography Imaging" J. Med. Chem., 36:855–862 (1993) Without Month.

Milius et al. "Synthesis and Receptor Binding of N–Substituted Tropane Derivatives. High–Affinity Ligands for the Cocaine Receptor" J. Med. Chem., 34:1728–1731 (1991) Without Month.

Milius et al., "[3H]–CFT, A High–Affinity Probe for the Cocaine Receptor" Amer. Chem. Soc. Abstract, 199:1 (1990) Without Month.

Neumeyer et al. "[$^{123}$I]–2β– Carbomethoxy–3β–(4–iodophenyl) tropane: High–Affinity SPECT Radiotracer of Monoamine Reuptake Sites in Brain" J. Med. Chem., 34:3144–3146 (1991) Without Month.

Patet et al. "A Cocaine Analog and a GBR Analog Label the Same Protein in Rat Striatal Membranes" Brain Res., 576:173–174 (1992) Without Month.

Reith et al. "Radiolabeling of Dopamine Uptake Sites in Mouse Striatum: Comparison of Binding Sites for Cocaine, Mazindol, and GBR 12935" Arch. of Pharmacol., 345:309–318 (1992) Without Month.

Ritz et al. "Cocaine Inhibition of Ligand Binding at Dopamine, Norepinephrine and Serotonin Transporters: A Structure–Activity Study" Life Sciences, 46:635–645 (1990) w/o Month.

Rubenstein "III Imaging With Photons" Scientific American, 1/88:1–14 (1988) w/o Month.

Scheffel et al. "In Vivo Labeling of Cocaine Binding Sites on Dopamine Transporters with [$^3$H] WIN 35,428" J. Pharmacol. & Exper. Therapeutics, 257:954–958 (1991) w/o Month.

Scheffel et al. Cocaine Receptors: In Vivo Labeling With $^3$H–(–)Cocaine, $^3$H–WIN 35,065–2, and $^3$H–WIN 35,428 Synapse, 4:390–392 (1989) w/o Month.

Spealman et al. "Self–Administration of the High Affinity Cocaine Analog 2β–Carbomethoxy–3β (4–Fluorophenyl) Tropane" Pharmacol. Biochem. & Behavior, 39:1011–1013 (1991) w/o Month.

Zakusov et al. "Pharmacology of New Tropan Derivatives" Pharmac. Ther., 32:327–337 (1987) w/o Month.

Isacson "Clinical and Preclinical PET Correlates of Parkinsonism with $^{11}$C–WIN 35,428" Annals of Neuro., 35:377–378 (1994) w/o Month.

Meyer et al. "Intravenously Administered Dopamine Transporter Site Radioligand is Not Significantly Retained in Mouse Substantia Nigra or Other Sites Outside of . . . " Annals of Neurology, 35:378–379 (1994) w/o Month.

Bergman et al., J. Pharmacol. Exp. Ther., 251:150–155 (1989) w/o Month.

Calligaro and Eldefrawi, J. Pharmacol. Exp. Ther., 243:61–68 (1987) w/o Month.

Calligaro and Eldefrawi, Membrane Biochem., 7:87–106 (1988) w/o Month.

Javaid et al., Science, 202:227–228 (1978) w/o Month.

Madras et al., FASEB J., 2:A1137 (1988) w/o Month.

Madras et al., ASP/ASPET Abstr., A197 (1988) w/o Month.

Madras et al., J. Pharmacol. Exp. Ther., 251:131–141 (1989) w/o Month.

Misra et al., Drug Alcohol Depend., 2:261–272 (1977) w/o Month.

Reith et al., Biochem. Pharmacol., 35:1123–1129 (1986) w/o Month.

Schoemaker et al., Naunyn–Schmiedeberg's Arch. Pharacol., 329:227–235 (1985) w/o Month.

Spealman et al., J. Pharmacol. Exp. Ther., 251:142–149 (1989) w/o Month.

Spealman et al., J. Pharmacol. Exp. Ther., 258:945–953 (1991) w/o Month.

Van Dyke et al., Science, 191:859–861 (1976) w/o Month.

Reith et al., Biochem. Pharmacol. 35:1123–1129 (1986) w/o Month.

Calligaro and Eldefrawi, J. Pharmacol. Exp. Ther. 243:61–68 (1987) w/o Month.

Calligaro and Eldefrawi, Membrane Biochem. 7:87–106 (1988) w/o Month.

Schoemaker et al., Naunyn–Schmiedeberg's Arch. Pharmacol. 329:227–235 (1985) w/o Month.

Madras et al., J. Pharmacol. Exp. Ther. 251:131–141 (1989) w/o Month.

Van Dyke et al., Science 191:859–861 (1976) w/o Month.

Misra et al., Drug Alcohol Depend. 2:261–272 (1977) w/o Month.

Javaid et al., Science 200:227–228 (1978) w/o Month.

Spealman et al., J. Pharmacol. Exp. Ther. 251:142–149 (1989) w/o Month.

Bergman et al., J. Pharmacol. Exp. Ther. 251:150–155 (1989) w/o Month.

Spealman et al., J. Pharmacol. Exp. Ther. 258:945–953 (1991) w/o Month.

Van der Zee et al., "A comparison of the inhibitory effects of aromatic substituted benzhydryl . . . into synaptosomal preparations of the rat brain", Neuropharmacology, 17(7), 483–90, 1978.

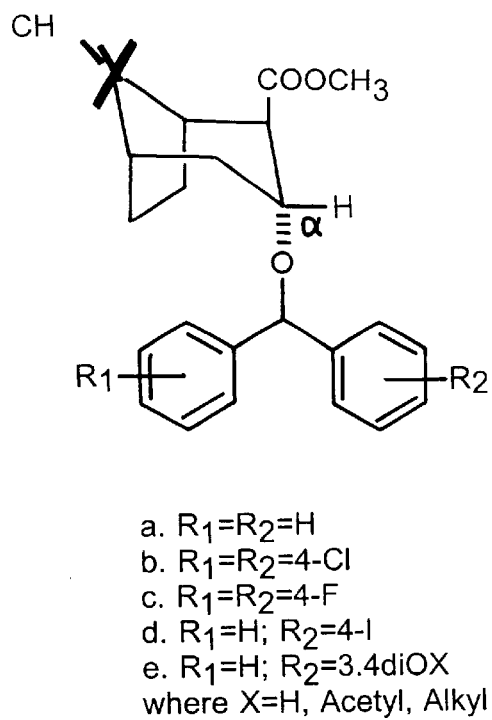
a. $R_1=R_2=H$
b. $R_1=R_2=4\text{-Cl}$
c. $R_1=R_2=4\text{-F}$
d. $R_1=H; R_2=4\text{-I}$
e. $R_1=H; R_2=3,4\text{diOX}$
where X=H, Acetyl, Alkyl
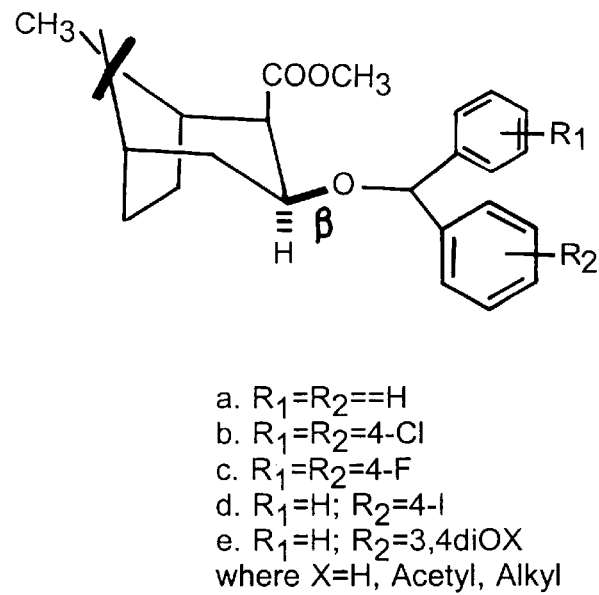
a. $R_1=R_2==H$
b. $R_1=R_2=4\text{-Cl}$
c. $R_1=R_2=4\text{-F}$
d. $R_1=H; R_2=4\text{-I}$
e. $R_1=H; R_2=3,4\text{diOX}$
where X=H, Acetyl, Alkyl
FIG. 8

BRIDGE-SUBSTITUTED TROPANES FOR METHODS OF IMAGING AND THERAPY

CROSS-REFERENCE TO RELATED APPLICATION

This application is a continuation-in-part of our earlier commonly owned co-pending application U.S. Ser. No. 08/548,271, filed Oct. 25, 1995, now abandoned which was a divisional of U.S. Ser. No. 08/111,141, filed Aug. 24, 1993 (now U.S. Pat. No. 5,506,359), which in turn was a continuation-in-part of U.S. Ser. No. 07/934,362, filed Aug. 24, 1992, now abandoned. Each of the above applications and any patents issuing on them are hereby incorporated by reference.

BACKGROUND OF THE INVENTION

The invention relates to cocaine analogues.

The abuse of cocaine is a health problem of national significance. Despite intensive study, there is still inadequate information about the neurochemical mechanisms mediating cocaine's detrimental effects and abuse liability or about drug therapies for cocaine abuse.

Recent studies have identified biologically relevant binding sites for cocaine in brain tissue of rodents (Reith et al., Biochem. Pharmacol. 35:1123–1129, 1986; Kennedy and Hanbauer, 41:172–178, 1983; Calligaro and Eldefrawi, J. Pharmacol. Exp. Ther. 243:61–68, 1987; Calligaro and Eldefrawi, Membrane Biochem. 7:87–106, 1988), humans (Schoemaker et al., Naunyn-Schmiedeberg's Arch. Pharmacol. 329:227–235, 1985), and nonhuman primates (Madras et al., FASEB J. 2:A1137, 1988; Madras et al., ASP/ASPET Abstr. A197, 1988; Madras et al., J. Pharmacol. Exp. Ther. 251:131–141, 1989). These sites, which are associated with monoamine uptake systems, can be labeled with [$^3$H] cocaine and have properties characteristic of a pharmacological receptor. First, the sites bind [$^3$H]cocaine saturably with affinities in the $10^{-6}$ to $10^{-6}$M range, concentrations comparable to those achieved in brain or plasma after peripheral administration of cocaine to animals or humans (Van Dyke et al., Science 191:859–861, 1976; Misra et al., Drug Alcohol Depend. 2:261–272, 1977; Javaid et al., Science 200:227–228, 1978). Second, the sites display stereoselectivity for (−)-cocaine over (+)-cocaine or its C-2 epimer pseudococaine (Madras et al., APS/ASPET Abstr. A197, 1988; Madras et al., J. Pharmacol. Exp. Ther. 251:131–141, 1989). Third, and perhaps most importantly, there is a high degree of correspondence between the relative potencies of various cocaine analogs for producing cocaine-like effects in vivo and relative binding affinities of the drugs for [$^3$H]cocaine binding sites in vitro. Specifically, the $ED_{50}$ values of cocaine and several cocaine analogs for producing behavioral stimulation (Spealman et al., J. Pharmacol. Exp. Ther. 251:142–149, 1989) or for maintaining self-administration in non-human primates (Bergman et al., J. Pharmacol. Exp. Ther. 251:150–155, 1989) parallel their $IC_{50}$ values for displacing [$^3$H]cocaine from binding sites in monkey brain (Madras et al., FASEB J. 2:A1137, 1988; Madras et al., J. Pharmacol. Exp. Ther. 251:131–141, 1989).

Although cocaine inhibits the uptake of dopamine, serotonin, and norepinephrine with similar potencies, [$^3$H] cocaine recognition sites on the dopamine transporter are particularly relevant to the behavioral effects of cocaine (Reith et al., Biochem. Pharmacol. 35:1123–1129, 1986; Madras et al., FASEB J. 2:A1137, 1988; Madras et al., J. Pharmacol. Exp. Ther. 251:131–141, 1989, Bergman et al., J. Pharmacol. Exp. Ther. 251:150–155, 1989; Spealman et al., J. Pharmacol. Exp. Ther. 251:142–149, 1989). Cocaine congeners and other drugs block behaviorally relevant [$^3$H] cocaine binding in monkey caudate-putamen with a rank order of potency that corresponds closely to their reported potencies for inhibiting uptake of dopamine but not norepinephrine or serotonin (Madras et al., J. Pharmacol. Exp. Ther. 251:131–141, 1989). Furthermore, selective norepinephrine or serotonin inhibitors do not produce the characteristic stimulant, reinforcing and interoceptive effects elicited by cocaine (Spealman et al., J. Pharmacol. Exp. Ther. 251:142–149, 1989; Spealman et al., J. Pharmacol. Exp. Ther. 258:945–953, 1991; Bergman et al., J. Pharmacol. Exp. Ther. 251:150–155, 1989). Together, these studies support the view that cocaine recognition sites associated with the dopamine transporter are important mediators of the behavioral effects of cocaine.

Further clarification of the mechanisms by which cocaine and related drugs alter behavior and maintain abuse will likely emerge from molecular characterization of cocaine receptor sites and imaging these sites in the brain. These studies have been hampered, however, by the relative inefficiency of [$^3$H]cocaine as a radioligand and the lack of versatile probes to elucidate the molecular properties of the receptor complex. In particular, [$^3$H]cocaine binds to the receptor with modest affinity in all brain regions studied ($K_{0.50} \approx 300$ nM) and dissociates rapidly. This modest affinity of [$^3$H]cocaine (25–30 Ci/mmole) make it a relatively poor tag for imaging cocaine receptors, either in vitro or in vivo.

Drug therapies for cocaine abuse also are needed, and therapeutic agents based on cocaine congeners are proposed.

There is also a need for suitable agents and procedures to diagnose neurodegenerative disorders, such as Parkinson's disease. In particular, exclusion of Parkinson's disease as the cause of symptoms at an early stage may be useful information in diagnosing other conditions such as Alzheimer's disease. In addition, early diagnosis of Parkinson's disease facilitates the introduction of prophylactic drug therapy (e.g., deprenyl administration) prior to the onset of symptoms.

Finally, there is a need for agents that treat other disorders by targeting brain monamine neurotransporters.

SUMMARY OF THE INVENTION

It has been generally assumed that nitrogen should be incorporated into drugs used to target brain monoamine neurotransporters, e.g., agents for diagnosing or treating cocaine addiction, Parkinson' disease, Attention Deficit Hyperactivity Disorder, depression, and other conditions. We have determined that compounds lacking nitrogen can be effective for these purposes. In particular, we have discovered bridge-substituted tropanes and uses for those compounds described below.

One aspect of the invention features a compound having one of the following general formulas A., B, C, or D:

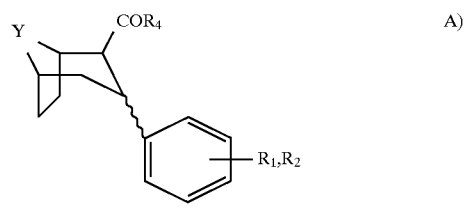

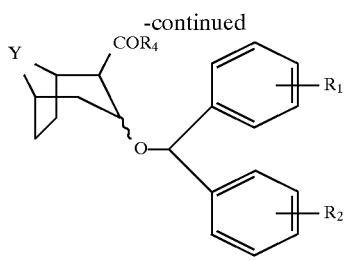

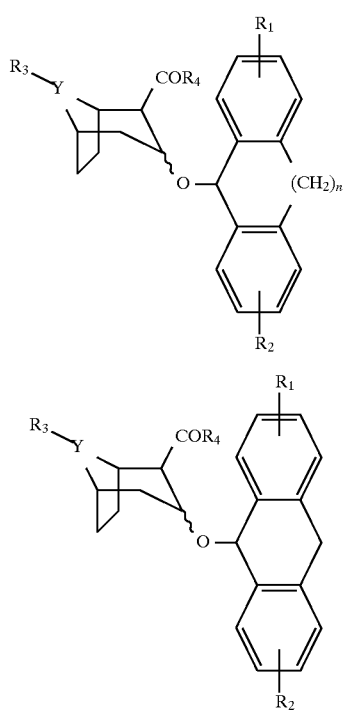

In those formulas:

Y is C, O, S, SO, or $SO_2$; and $R_1$ and $R_2$ are both 4-F, 4-Cl, 3,4-diCl, 4-I, H, 3,4-diOH, 3,4-diOAc, or 3,4-diOCH$_3$; or $R_1$ is H and $R_2$ is 4-F, 4-Cl, 4-I, 2-F, 2-Cl, 2-I, 3-F, 3-Cl, 3-I, 3,4-diCl, 3,4-diOH, 3,4-diOAc, or 3,4-diOCH$_3$; or $R_1$ is H and $R_2$ is 3-OH-4-Cl, 3-OH-4-F, 3-Cl-4-OH, or 3-F-4-OH; or $R_1$ is the same as $R_2$ and both are chosen from 3-OH-4-Cl, 3-OH-4-F, 3-Cl-4-OH, or 3-F-4-OH; or $R_1$ is not the same as $R_2$ and both are chosen from 3-OH-4-Cl, 3-OH-4-F, 3-Cl-4-OH, or 3-F-4-OH; and wherein $R_4$ is $CH_3$, $CH_3CH_2$, $(CH_3)_2CH$, $CH_3(CH_2)_n$, $(CH_2)_nC_6H_4X$, $C_6H_4X$, $C_6H_5$, $OCH_3$, $OCH_3CH_2$, $OCH(CH_3)_2$, $OC_6H_5$, $OC_6H_4X$, $O(CH_2)_nC_6H_4X$, or $O(CH_2)_n CH_3$, wherein X is Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$ or $C(CH_3)_3$, wherein n is between 0 and 6 inclusive.

Those formulas cover compounds in which the linkage at the 2- and 3- position can be (independently) α or β. They also cover compositions enriched in either the R enantiomer or in the S enantiomer, as well as racemic mixtures of those enantiomers.

In more detailed embodiments, Y is O; the linkage at the 3-position is α; and each $R_1$ and $R_2$, independently, is Cl, I, or F. In another instance, $R_4$ is $OCH_3$; and Y is C; and $R_1$ and $R_2$ are both F or both I.

In a preferred embodiment, the compound is labelled with a radioactive or fluorescent label; preferable labels include $^3H$, $^{11}C$ (e.g., on the aromatic ring substituent(s)) $^{123}I$ or $^{125}I$ or $^{18}F$ (e.g., on the aromatic ring(s) of the C-3 substituent.

These compounds have several uses based on the finding that cocaine recognition sites are localized on the dopamine transporter, which itself is localized on dopamine nerve terminals. Uses for drugs that bind to these sites include (i) imaging probes for dopamine transporter/cocaine binding sites, (ii) imaging probes for neurodegenerative disorders, (iii) drug therapies for cocaine abuse, and (iv) drug therapies for neurodegenerative disorders such as Parkinson's disease.

The compounds may therefore be used as cocaine substitutes to treat cocaine addiction and, when detectably labelled, may be used as tags to assay the number of cocaine receptors in the brain. Because such receptors are present in decreased number in the brains of patient's afflicted with Parkinson's disease, such synthetic cocaine analogs facilitate a method of in vivo imaging for diagnosing this disease. In addition, such analogs, by virtue of their ability to inhibit dopamine transport and increase synaptic dopamine levels may serve as therapeutics for Parkinson's disease.

Additionally, because of the unique anatomical location of the cocaine recognition sites, a high affinity probe for imaging of these sites in vivo in the brain may be carried out using, e.g., PET or SPECT imaging. Such imaging is useful for the purposes of (i) assaying cocaine receptors in chronic cocaine users and in individuals exposed to cocaine prenatally, (ii) assaying the receptor occupancy of potential cocaine therapeutics, and (iii) assaying cocaine receptors in individuals that abuse other drugs. Such imaging is also useful for monitoring the occupancy of the dopamine transporter by established and novel drugs that are targeted to and/or bind to these sites; these drugs include, but are not limited to, antidepressants (e.g., bupropion), attention deficit disorder/hyperactivity syndrome therapies (e.g., methylphenidate or pemoline), and dopamine uptake inhibitors useful for treating Parkinson's disease (e.g., benztropine, also termed cogentin). Finally, such imaging agents are useful for diagnosing or monitoring Parkinson's disease, a neurological disorder characterized by the degeneration of dopamine nerve terminals.

Apart from the uses described above, cocaine analogs may also provide alternatives to cocaine in the pharmacological management of cocaine abuse. The development of cocaine drug therapies which can be readily administered on an out-patient basis under controlled conditions may diminish the illicit drug trade, reduce the probability of AIDS transmission by frequent intravenous dose administration of cocaine, and enable abusers greater access to treatment programs. In a related aspect, the compounds of the invention may be formulated as therapeutic compositions, essentially including the compound in a pharmaceutically acceptable carrier.

Another object of the invention was to develop compounds useful for cocaine drug therapy. Such compounds include cocaine-like drugs preferably having a longer onset time, a longer duration of action, and a diminished abuse liability relative to cocaine; compounds described herein are expected to have such properties. The need also exists for cocaine antagonists which preferably bind sites normally bound by cocaine but without inhibiting dopamine transport. The compounds of the invention which lack a ring nitrogen or possess a catechol moiety likely provide such useful cocaine antagonists. A number of the compounds described herein are useful for the treatment of Parkinson's disease and similar neurodegenerative disorders.

Thus, in another aspect, the invention features a method of treating cocaine addiction in a mammal, involving administering a therapeutic composition of the invention to the mammal.

In still another aspect, the invention features a method of selectively imaging cocaine binding regions of the central nervous system of a human patient, involving administering to the central nervous system a detectably labelled compound of the invention or CFT and detecting the binding of that compound to CNS tissue (e.g., by position emission tomography (PET) or single-photon emission computed tomography (SPECT)).

In a fifth aspect, the invention features a method of detecting parkinsonism in a human patient, involving administration to the patient of a detectably labelled compound of the invention or CFT.

In a sixth aspect, the invention features a method of treating a neurodegenerative disorder (e.g., Parkinson's disease) characterized by monoamine nerve terminal degeneration in a human patient involving administration to the patient of a therapeutic compound of the invention.

DETAILED DESCRIPTION OF THE DRAWINGS

FIGS. 1A, 1B, and 1C are graphs showing the relationship between drug potencies at [$^3$H]CFT binding sites and drug potencies (FIG. 1A) at [$^3$H]cocaine binding sites; (FIG. 1B) at the dopamine transporter in the caudate-putamen; and (FIG. 1C) at the dopamine transporter in the nucleus accumbens.

FIG. 8 depicts various benzotropine analogs.

DESCRIPTION OF THE PREFERRED EMBODIMENT

I. NOVEL COCAINE ANALOGS

Figure 5:
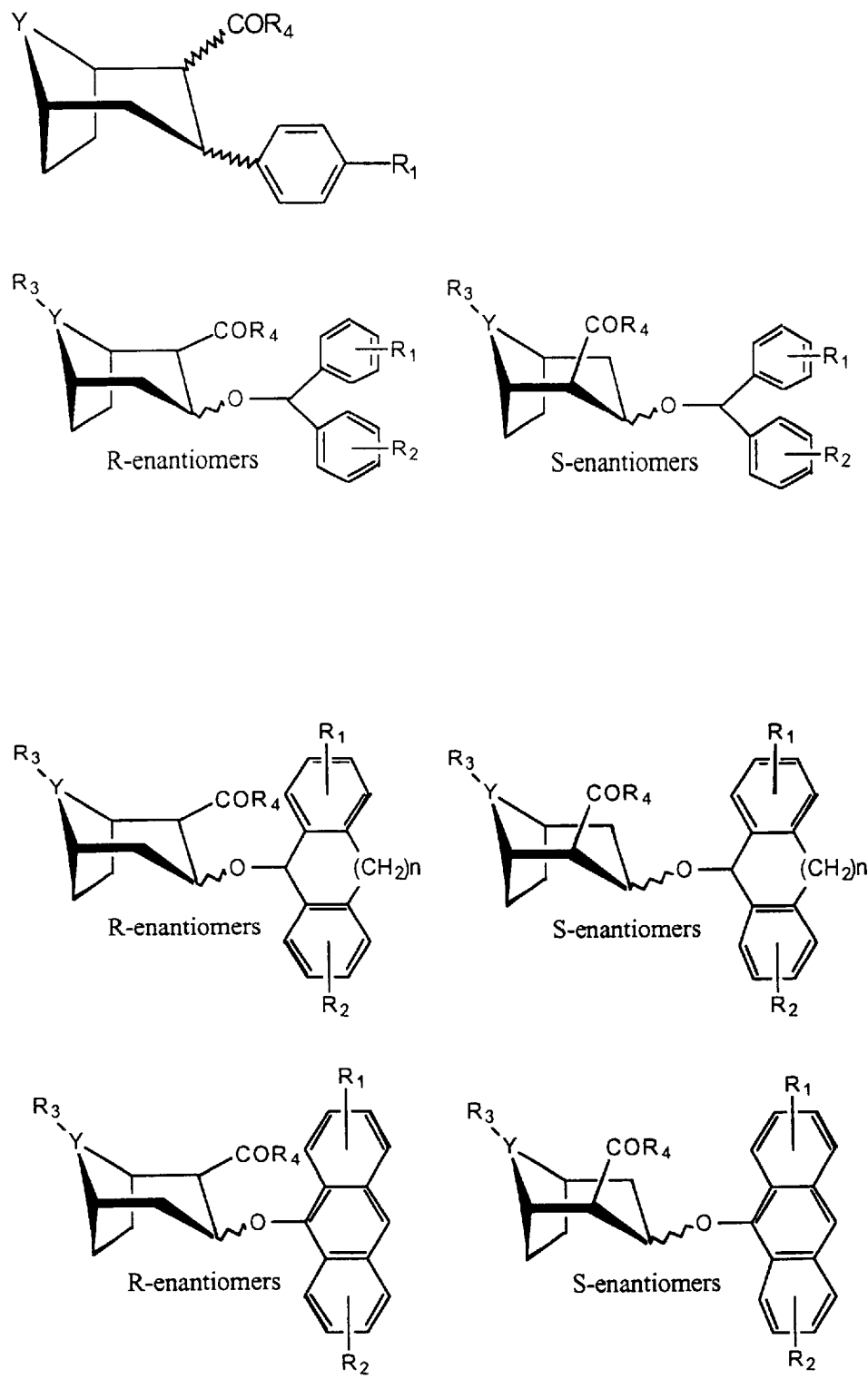
FIG. 5 shows R and S enantiomers of various compounds.

General formulas for compounds of the invention are given above and in FIG. 5. Preferred compounds are those in which Y=C, O, S; and SO, SO$_2$, linkage at 2 is α- or β-, linkage at 3 is α- or β-. The molecules may be racemic, and/or R-enantiomers, and/or S-enantiomers, n=0,1,2, R$_1$ and R$_2$ are both 4-F, 4-Cl, 3,4-diCl, 4-I, H, 3,4-diOH, 3,4-diOAc, 3,4-diOCH$_3$, or R$_1$=H and R$_2$=4-F, 4-Cl, 4-I, 2-F, 2-Cl, 2-I, 3-F, 3-Cl, 3-I, 3,4-diCl, 3,4-diOh, 3,4-diOAc, 3,4-diOCH$_3$, or R$_1$=H and R$_2$=3-OH-4-Cl, 3-OH-4-F, 3-Cl-4-OH, 3-F-4-OH, or R$_1$=R$_2$=3-OH-4-Cl, 3-OH-4-F, 3-Cl-4-OH, 3-F-4-OH, or R$_1$ not=R$_2$; both=3-OH-4-Cl, 3-OH-4-F, 3-Cl-4-OH, 3-F-4-OH where X=Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, C(CH$_3$)$_3$ where n=0–6. R$_4$=CH$_3$, CH$_3$CH$_2$, CH$_3$(CH$_2$)$_n$(CH$_2$)$_n$C$_6$H$_4$X, C$_6$H$_4$X, C$_6$H$_5$, OCH$_3$, OCH$_3$CH$_2$, OC$_6$H$_5$, OC$_6$H$_4$X, OC$_6$H$_3$XY, OCH(CH$_3$)$_2$, CHCH$_2$.

Those compounds can be evaluated to optimize activity according to the techniques described below. Desirable properties included high affinity and high selectivity for the dopamine transporter (preferably in the picomolar-low nanomolar range). The affinity and selectivity of the congener is preferably at least comparable to that of cocaine so that the full spectrum of biologically relevant cocaine recognition sites throughout the brain may be monitored. The compounds of the invention are examples of such improved imaging probes.

II. Techniques for evaluating and using cocaine mimics

In reviewing the claimed compounds and their uses, it is helpful to refer to experiments using two known compounds which have been studied for their ability to mimic cocaine binding in the brain, and to mimic the in vivo effects of cocaine. These compounds are: a) 2β-carbomethoxy-3β-(4-fluorophenyl)tropane or "CFT"; it is also designated "WIN 35,428"; and b) 2β-carbomethoxy-3β-(4-iodophenyl)tropane or "CIT".

The cocaine receptor-binding assays, and the other protocols for testing the ability of CFT to mimic cocaine, can also be used for evaluating the other cocaine analogs described below. Those skilled in the art will understand that the procedures detailed below for CFT are generally applicable to other cocaine analogs discussed below.

A. Binding Studies

Specifically, in early studies, the binding properties of the cocaine congener [$^3$H]CFT were determined in tissue homogenates and compared with those of [$^3$H]cocaine (Madras et al., Mol. Pharmacol. 36:518–524, 1989). All studies were conducted in monkey brain caudate-putamen for two reasons. First, this dopamine-rich brain region has the highest density of [$^3$H]cocaine receptors in the brain, and dopamine has been implicated in mediating the effects of cocaine. Second, primates are consistently used to test diagnostic imaging agents and to test for cocaine-like drugs and drug therapies for Parkinson's disease. These studies indicated that [$^3$H]CFT and [$^3$H]cocaine binding in monkey caudate-putamen were similar in the following respects:

(1) The density of [$^3$H]CFT binding sites (Bmax: 388 pmol/g) was similar to the density of [$^3$H]cocaine binding sites (Bmax: 471 pmol/g).

(2) Both [$^3$H]cocaine and [$^3$H]CFT labeled high- and low-affinity binding components, with the high-affinity component constituting approximately 10% of the total number of sites.

(3) NaCl was necessary for specific binding of [$^3$H]CFT and [$^3$H]cocaine.

(4) Both [3H]CFT and [3H]cocaine were inhibited stereoselectively by the enantiomers of cocaine and pseudococaine and by the diastereoisomers of WIN 35,065-2.

Figure 1A:
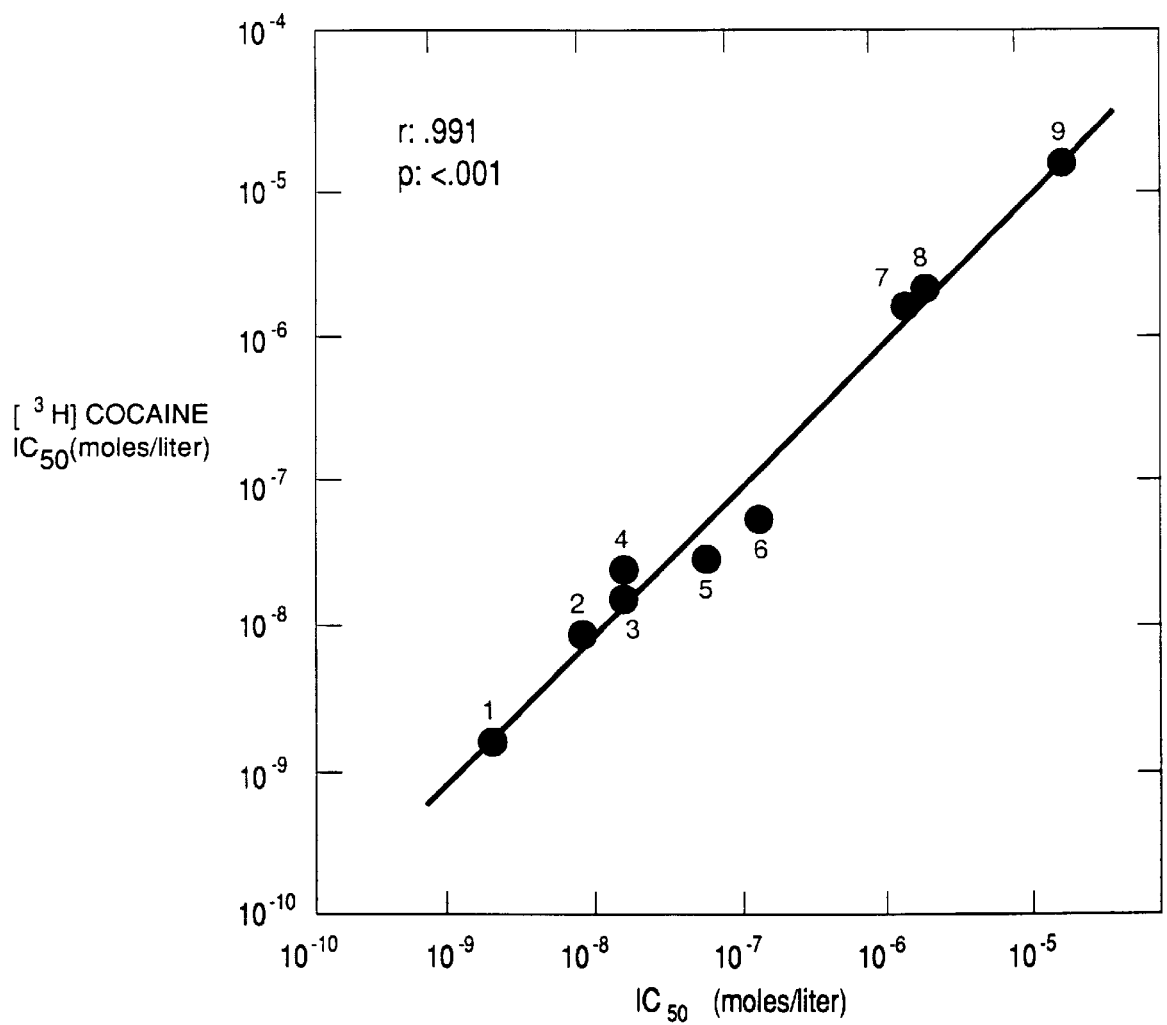

(5) A high positive correlation between the potencies of drugs for inhibiting specifically bound [$^3$H]CFT and [$^3$H]cocaine was clearly demonstrated (0.99; p<0.001; FIG. 1A).

Figure 1B:
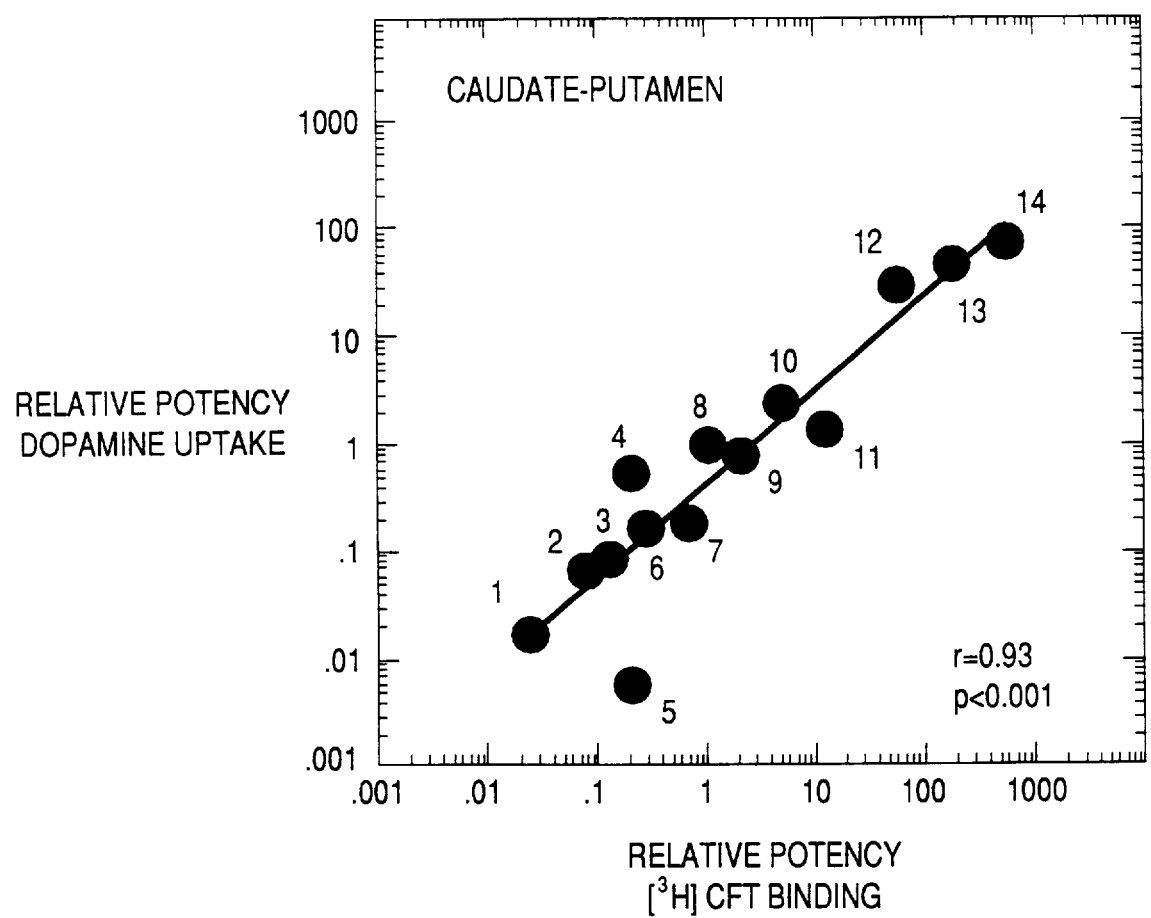
Figure 1C:
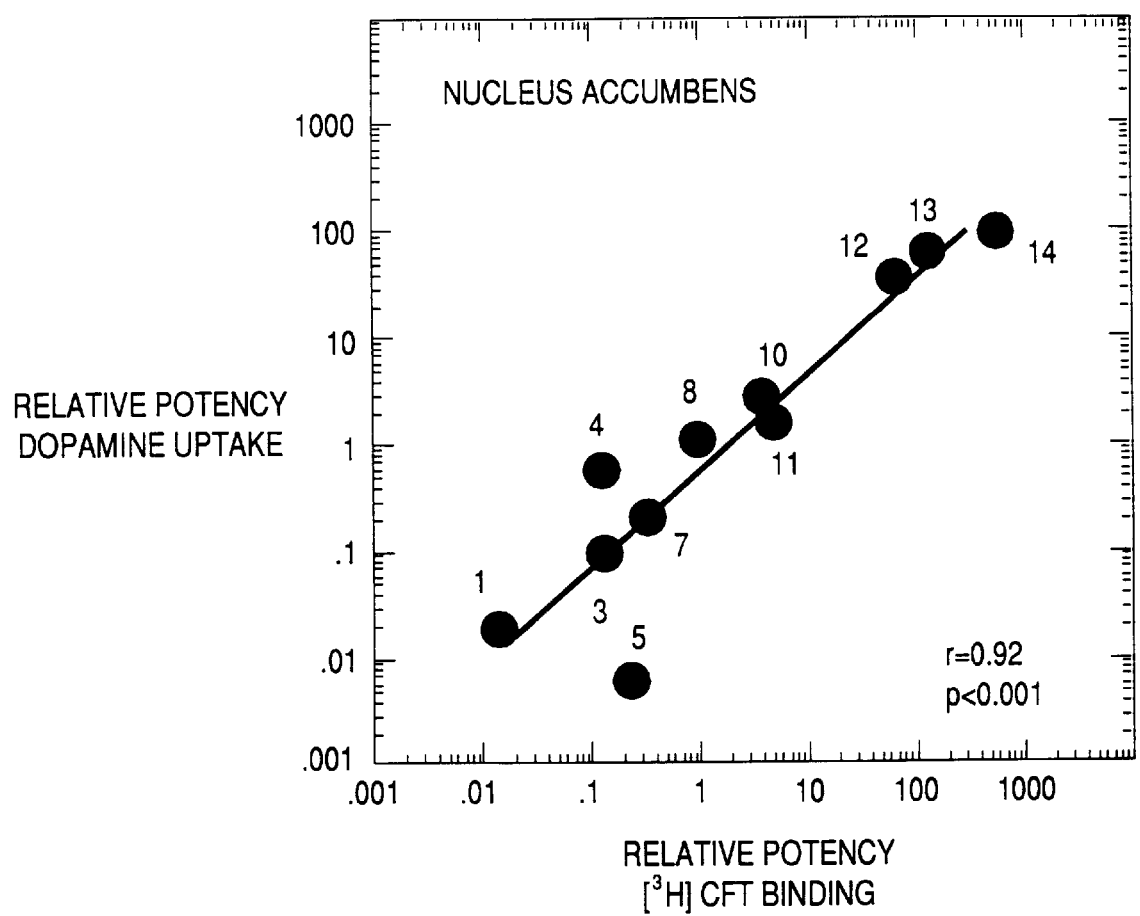

(6) A high positive correlation was found between the relative potencies of drugs for inhibiting [$^3$H]CFT or [$^3$H]cocaine binding and for inhibiting dopamine uptake (FIG. 1B).

Figure 2A:
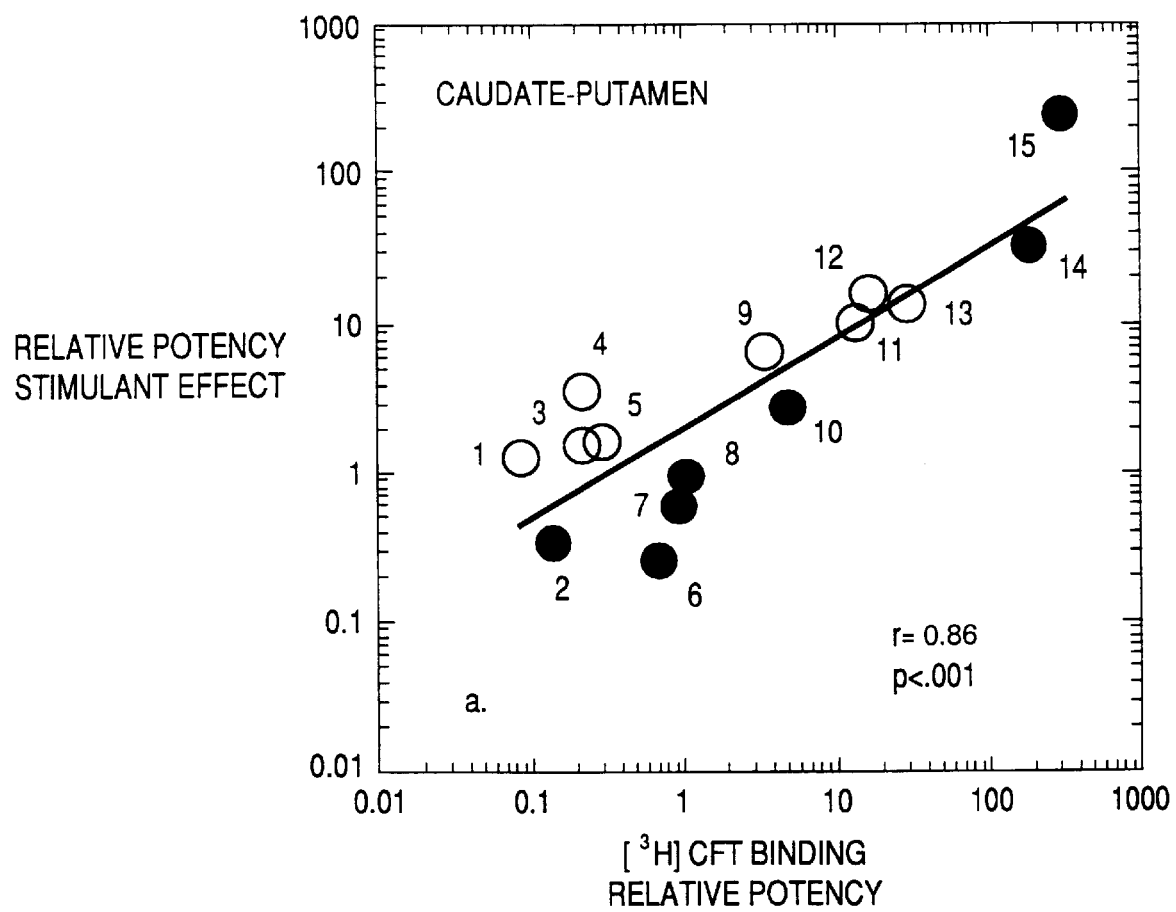
FIGS. 2A and 2B are graphs showing the relationship (FIG. 2A) between [$^3$H]CFT binding and psychomotor stimulation and (FIG. 2B) between [$^3$H]CFT binding and maintenance of drug self-administration.
Figure 2B:
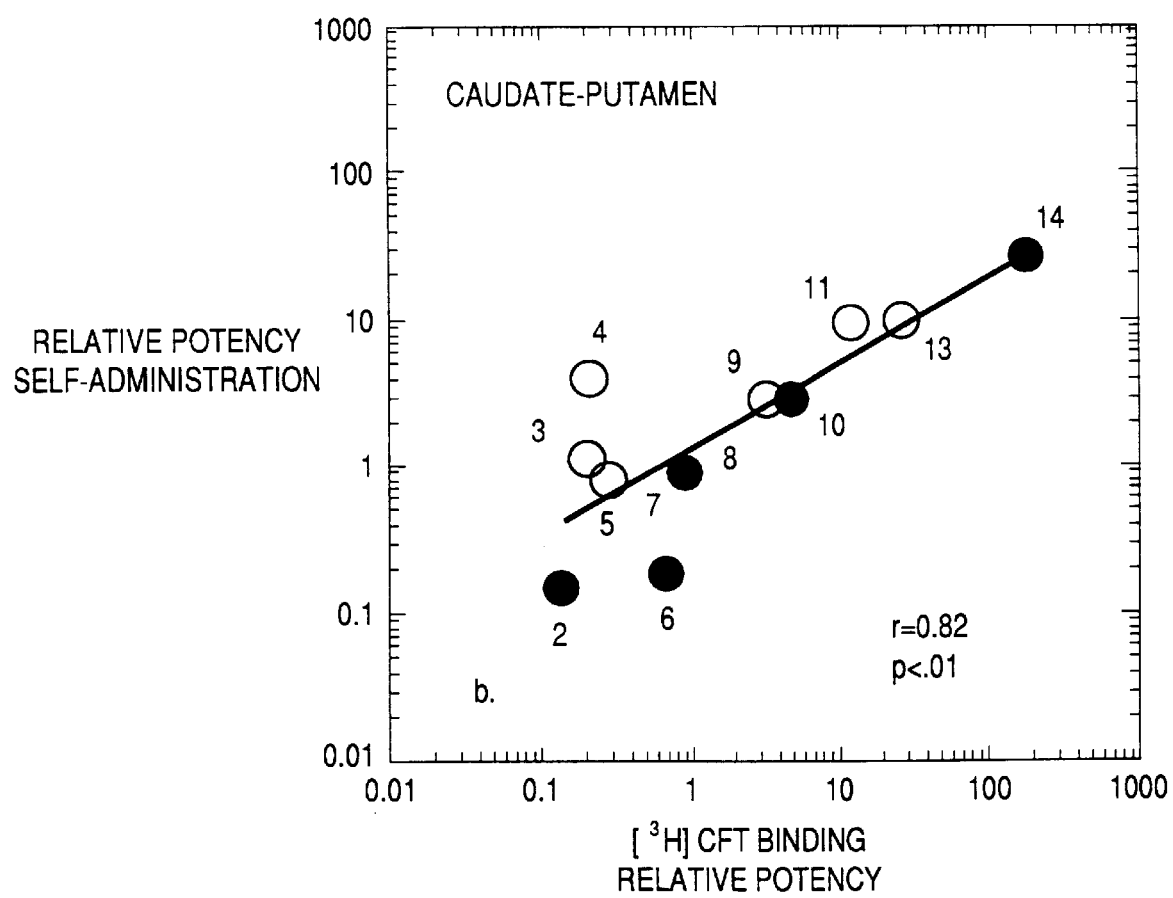

(7) The relative potencies of cocaine analogs and other monoamine uptake inhibitors for inhibiting [$^3$H]CFT binding in monkey caudate-putamen corresponded closely to their relative potencies for producing behavioral stimulation (FIG. 2A) and for maintaining intravenous drug self-administration (FIG. 2B). This high degree of correspondence supports the view that in caudate-putamen, the pharmacological profiles of [$^3$H] CFT and [$^3$H]cocaine are virtually identical and that [$^3$H]CFT labels behaviorally relevant cocaine receptors.

Figure 3:
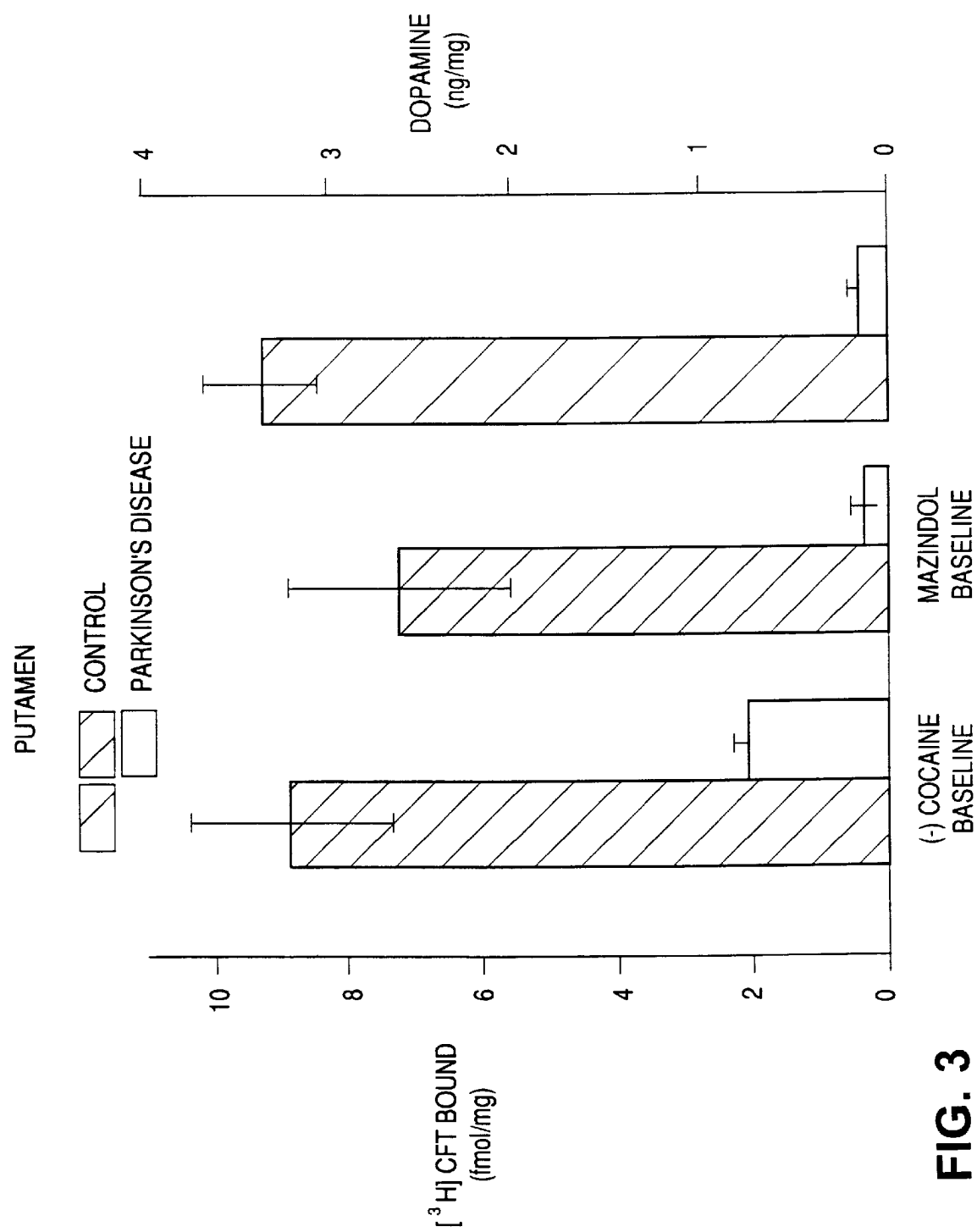
FIG. 3 is a bar graph showing a comparison between the amount of [$^3$H]CFT bound in normal and Parkinson's-diseased human putamen and the relationship to dopamine levels.
Figure 4:
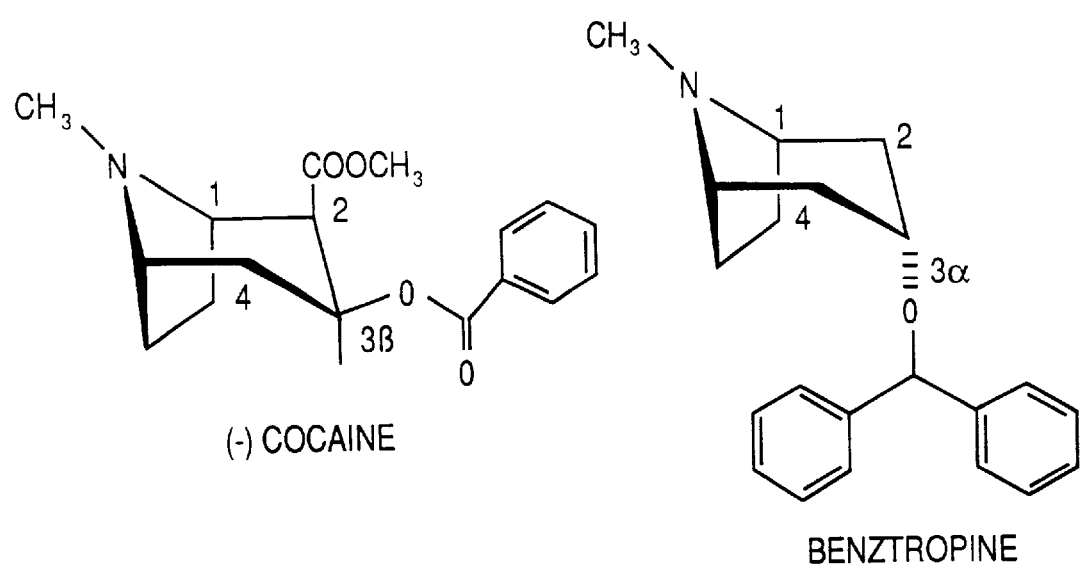
FIG. 4 shows the structure of (−)cocaine and benztropine to illustrate the stereospecificity of those compounds at the 3 position.

Depletion of [$^3$H]cocaine binding sites in post-mortem Parkinson's diseased putamen has been attributed to the pre-synaptic location of cocaine binding sites associated with the dopamine transporters (Schoemaker et al., Naunyn-Schmiedeberg's Arch. Pharmacol. 329:227–235, 1985). [$^3$H]CFT binding sites are severely depleted in post-mortem human Parkinson's diseased caudate-putamen using either tissue homogenates (FIG. 3) or tissue sections to monitor [$^3$H]CFT binding. These results suggest that CFT is a suitable marker for Parkinson's disease (Madras et al., Soc. Neurosci. Abst. 16:14, 1991; Kaufman and Madras, Synapse 9:43–49, 1991).

Moreover, the affinity of [$^3$H]CFT was higher and its dissociation rate slower than that of [$^3$H]cocaine. Improvements in both parameters were essential for detailed mapping and characterization of cocaine binding sites in the brain. The affinity of [$^3$H]CFT ($K_{0.50}$: 16.0 nM) was 18 times higher than that of [$^3$H]cocaine ($K_{0.80}$: 283 nM) and the dissociation rate considerably slower. Although unanticipated, [$^3$H]CFT offered other advantages over [$^3$H] cocaine. A higher degree of reproducibility using [$^3$H]CFT enabled previously unrecognized differences in the binding of drugs to become apparent. For example, competition curves for certain cocaine congeners and other drugs (e.g., CFT, cocaine, and (−)-norcocaine) were shallow (0.61–0.89), reached full displacement of [$^3$H]CFT and were characterized by at least two binding components. In contrast, competition curves for monoamine uptake inhibitors structurally distinct from cocaine (e.g., Lu 19-005, GBR 12909 and bupropion) were steeper (0.94–1.1), plateaued at levels corresponding to about 90–93% and were characterized by a single binding component. Furthermore, the level of non-specific binding of [$^3$H]CFT was lower than that of [$^3$H]cocaine. The low level of non-specific binding suggested that [$^3$H]CFT and other radiolabeled forms of CFT would be useful probes for imaging cocaine recognition sites and dopamine terminals and dopamine terminals in vitro and in vivo.

B. Behavioral Effects

To determine whether CFT also mimicked cocaine's behavioral effects in vivo (specifically the reinforcing and interoceptive effects), squirrel monkeys were trained to respond under a second order schedule of i.v. drug self-administration (see detailed description below). These studies demonstrated that CFT was approximately six times more potent than cocaine in maintaining responding. The potency relationships were similar to the potency relationships for cocaine and CFT for inhibiting [3H]CFT or [$^3$H] cocaine binding and for inhibiting dopamine uptake. The results were consistent with the view that the reinforcing effects of cocaine are mediated by cocaine recognition sites associated with the dopamine uptake system.

The subjective (interoceptive) effects of cocaine were studied in monkeys through the use of a drug discrimination procedure. This procedure was used to determine whether CFT produced a stimulus cue comparable to that of cocaine. Squirrel monkeys were trained to discriminate cocaine (0.3–0.56 mg/kg) from saline using a two-level choice procedure. CFT fully generalized to the cocaine cue, and their potency relationships relative to cocaine corresponded to the potency relationships for inhibiting [$^3$H]CFT binding sites in vitro. These results indicated that the subjective effects of CFT and cocaine were similar again suggesting that [$^3$H]CFT represented a useful probe for characterizing behaviorally relevant cocaine binding sites.

C. Distribution in Brain

To identify the distribution of cocaine recognition sites in the brain, autoradiographic techniques were utilized. Such techniques were particularly appropriate for this purpose because they are 100–1,000 times more sensitive than radioreceptor assays conducted in tissue homogenates. The moderately high affinity, slow dissociation, and low level of non-specific binding of [$^3$H]CFT made this congener particularly well suited for autoradiography and for imaging. Three sequential procedures: parametric studies, in vitro autoradiographic techniques, and ex vivo autoradiographic techniques were conducted in tissue sections of squirrel monkey brains. It should be noted that the pharmacological specificity of [$^3$H]CFT binding sites in squirrel monkey and cynomolgus striatum are virtually identical.

In order to characterize binding sites for [$^3$H]CFT in tissue sections, competition experiments were conducted using a fixed concentration of [$^3$H]CFT (3 nM) and a range of concentrations of (−)-cocaine, (+)-cocaine, CFT, Lu 19-005, GBR 12909, bupropion and citalopram. The $IC_{50}$ values for the drugs in tissue sections corresponded closely with their reported $IC_{50}$ values in monkey caudate-putamen membranes (r: 0.99; p<0.001), suggesting that [$^3$H]CFT binding is similar in the two preparations. The pharmacological specificity of [$^3$H]CFT binding sites in substantia nigra and zona incerta were similar.

After establishing suitable conditions for autoradiography, systematic mapping of cocaine recognition sites were conducted in squirrel monkey brain at nine anterior—posterior levels. Tissue sections were incubated alone, or in the presence of excess (−)-cocaine to determine total and nonspecific binding of [$^3$H]CFT, respectively. High densities of [$^3$H]CFT binding were present in the dopamine-rich brain regions, including the caudate nucleus, putamen, nucleus accumbens, and olfactory tubercle. In each of these brain regions, specific binding was >90% of total binding. Intermediate densities of [$^3$H]CFT binding were detected in substania nigra, zona incerta, amygdala, and the hypothalamus. Low, though measurable, levels of [$^3$H]CFT binding were observed in the bed nucleus of the stria terminalis, the ventral tegmental area, the medial preoptic area, the pineal, the hippocampus, and the thalamic central nuclei. Near background levels were found in the white matter, cerebellum, globus pallidus, and cortical regions See FIGS. 4a-A through 4a-F of the '359 patent referenced above. The distribution and density of [$^3$H]CFT binding sites closely paralleled the distribution of $D_1$ and $D_2$ dopamine receptors and the concentration of dopamine in primate brain, mediating the behavioral effects of cocaine (Kaufman et al., Synapse, supra, 1991).

From the in vitro autoradiographic studies, two conclusions were drawn: (a) cocaine receptors labelled by [$^3$H]CFT distributed primarily to dopamine-rich brain regions and (b) the highly circumscribed distribution and low level of non-specific binding of [$^3$H]CFT further supported the development of CFT as a PET imaging ligand for cocaine receptors in vivo. However, as the distribution pattern of a probe in vitro may not necessarily reflect its distribution in vivo, it was necessary to determine whether similar conclusions could be drawn using ex vivo autoradiographic techniques. The ex vivo autoradiographic distribution of [$^3$H]CFT was determined following intravenous administration of [$^3$H]CFT (1.0 or 2.5 nmol/kg) to squirrel monkeys. See FIGS. 4b- through 4bL of the '359 patent referenced above. Brain sections from several A-P levels were exposed to [³H]-sensitive film. The resulting autoradiograms revealed binding of [³H] CFT primarily in dopamine-rich brain regions: caudate, putaman>nucleus accumbens/olfactory tubercla, stria terminalis>substantia nigra>hypothalamus. Several regions such as cortex and thalamus displayed more prominent binding in vivo than in vitro. Nevertheless, the ex vivo labeling of brain regions by [³H]CFT corresponded closely to the in vitro autoradiographic pattern.

At the time these studies were completed, a higher affinity iodinated analog of [³H]CFT, [¹²⁵I]RTI-55 (i.e., CIT, 2β-carbomethoxy-3β-(4-iodophenyl)tropane; Dupont-NEN), became available. [¹²⁵I] RTI-55 labels sites in the caudate putamen with an approximately 10 fold higher potency than [³H]CFT. This ligand was also tested by ex vivo autoradiography as an imaging probe. Experiments carried out as described above revealed that highest densities of [¹²⁵I]RTI-55 were detected in the caudate-putamen, and moderately high densities also were found in the thalamus, cortex and brain stem nuclei. The results indicated that although both probes labeled dopamine-rich brain areas, [¹²⁵I]RTI-55 labeled sites in addition to those recognized by [³H]CFT. The additional sites labeled by [¹²⁵I]RTI-55 are associated with the serotonin transporter (Kaufman et al., Soc. Neurosci. Abst., 1991).

In a collaborative study with the PET imaging group at the Massachusetts General Hospital, a PCR-I camera was used to conduct preliminary PET imaging studies with [¹¹C]CFT in cynomolgus and squirrel monkeys in order to determine the distribution and kinetic properties of the ligand. The monkeys were injected with [¹¹C]CFT (Sp. act.: 400–700 Ci/mmol, 3–9 μg, 0.5–1 ml), arterial blood samples were collected, and dynamic imaging was carried out for 90 minutes. Images showed high uptake of [¹¹C]CFT in the caudate-putamen with a resulting striatal-to-cerebellar ratio of >4.0 at 58 min. Mazindol and other dopamine uptake inhibitors displaced bound [¹¹C]CFT from the striatum. [¹¹C]CFT binding was reduced in MPTP-treated Parkinsonian monkeys and depletion was found in asymptomatic monkeys. These results further suggest the use of [¹¹C]CFT to monitor Parkinson's disease (Hantraye et al., Neuro. Reports 3:265–268, 1992).

Results from the PET imaging studies were sufficiently encouraging to support further evaluation of CFT as a potential imaging probe for human brain. In order to determine whether [³H]CFT labels sites associated with the dopamine transporter, the binding of [³H]CFT to homogenates of human caudate nucleus and putamen, was characterized. [³H]CFT binding was saturable, stereoselective, and inhibited by drugs with a rank order of potency: Lu 19-005>CFT, mazindol, GBR 12909>(-)-cocaine >bupropion>(+)-cocaine, that was identical with that of cocaine receptors associated with the dopamine transporter in monkey caudate-putamen.

II. Synthesis

To prepare the compounds of the invention which lack a ring nitrogen, the following procedures may be utilized.

Synthesis of 2β-Carboxymethyl-3β-arylbicyclo [3.2.1]octanes.

To prepare the oxa, thia, and carbo analogs of CFT, the following synthetic procedures may be used.

Figure 6:
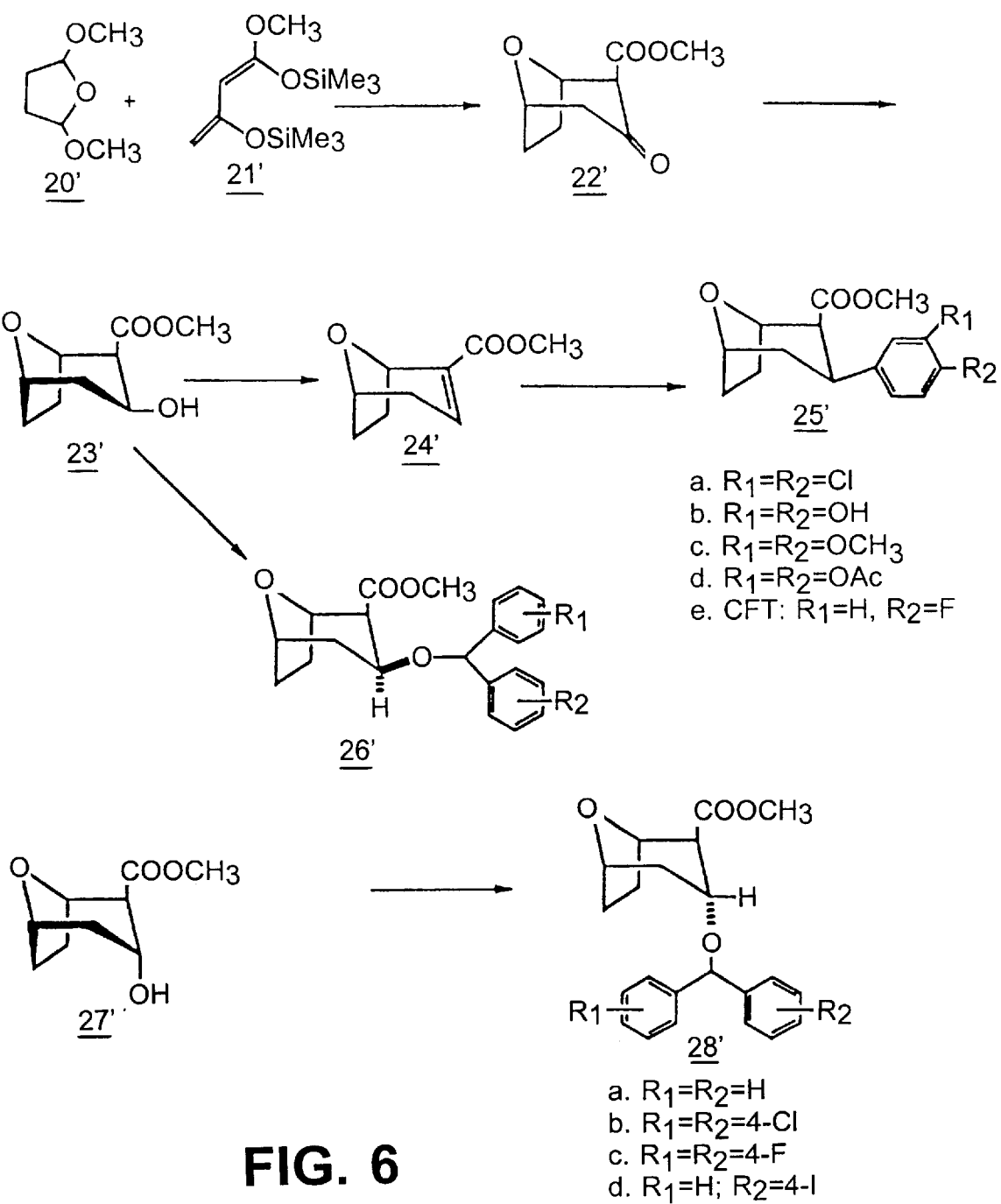
FIG. 6 shows one synthetic scheme for the preparation of analogs of the invention which lack a nitrogen in the tropane ring.
Figure 7:
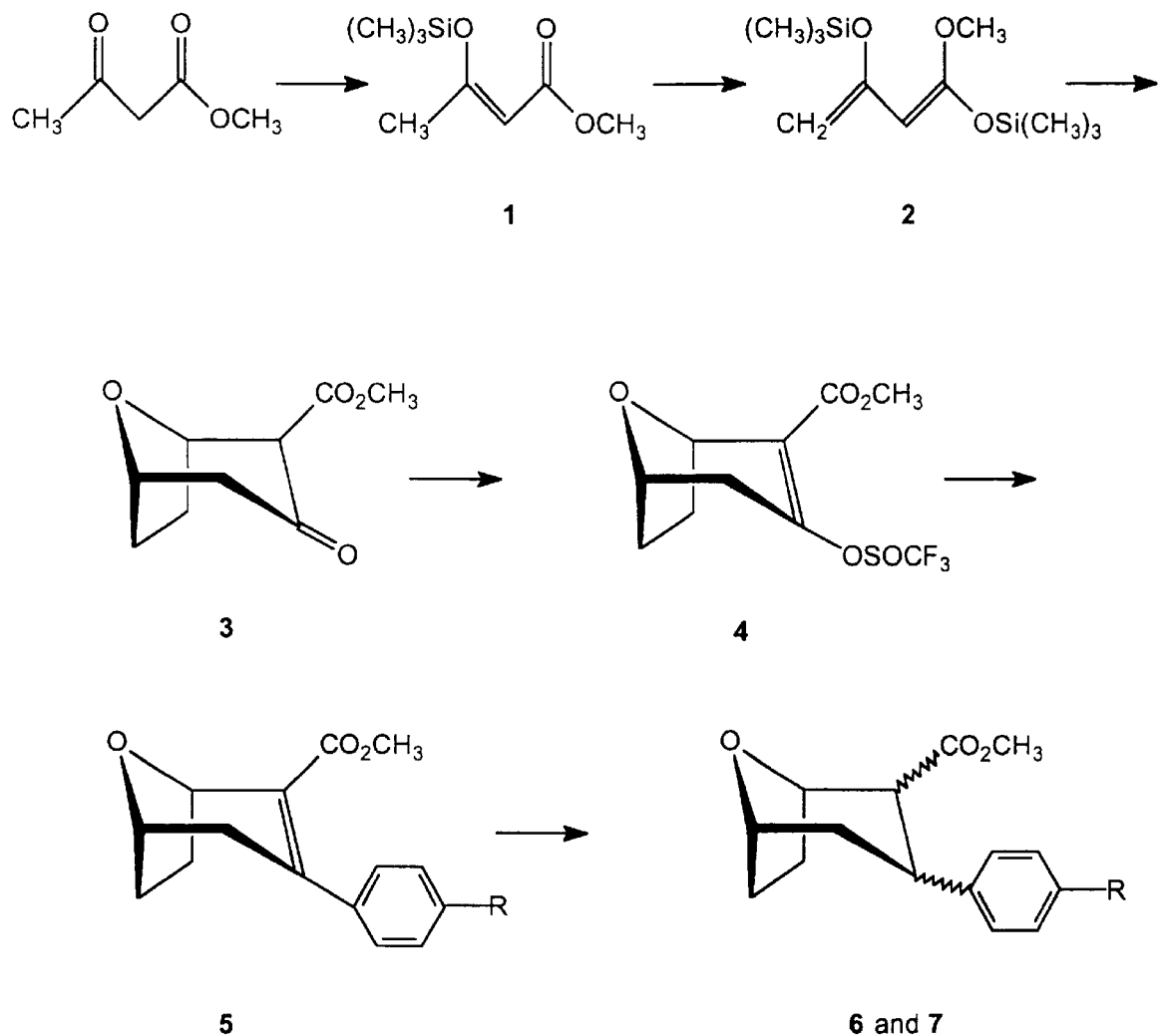
FIG. 7 shows another synthetic scheme for the preparation of analogs of the invention which lack a nitrogen in the tropane ring.

Initially, compound 22' is prepared, preferably as shown in FIG. 6 or 7 (where it is given the number 3). From that point, alternative synthesis routes are shown.

In FIG. 7, one synthesis of the 2-carbomethoxy-3-arylbicyclo[3.2.1]octanes utilizes the following route (see separate scheme provided). The essential feature of this alternative route is the reaction of a suitably substituted boronic acid with the intermediate triflate formed from 22' (FIG. 6). Thus, 22' is formed as described by Brownridge and Chan (Brownridge and Chan, Tetrahedron Letters, 46:4437, 1979)(the appropriate thia or carbon analogs are used as precursors for the synthesis of the thia and carbobicyclo[3.2.1]octanes). The enol triflate, 4, (See FIG. 7) is then formed by reaction with N-phenyltrifluoromethansulfonimide and sodium bistrimethylsilylamide. Coupling of the appropriate preformed aryl boronic acid is accomplished in the presence of tris (dibenzylideneacetone)dipalladium(0) to provide 5. Reduction of 5 with samarium iodide them provides the mixture of final products, 6 and 7. These are obtained as 2α and 2β and 3α and 3β substituted isomers and can be separated by careful column chromatography.

Separation of enantiomers can be accomplished as described earlier, or alternatively by formation of the camphor enolate ester of 3 and column chromatography of the diastereoisomers thus obtained. Hydrolysis of theseenantiomerically pure esters then provides enantiopure 3. Each enantiomer is then taken through the sequence described earlier to obtain the enantiopure products 6 and 7.

In FIG. 6, an alternative synthesis is shown, involving the reaction of a suitable aromatic Grignard reagent with the oxabicyclo[3.2.1]octene methyl ester 24'. This methyl ester is obtained by dehydration of the 3-hydroxy compound, 23', which is, in turn, obtained by reduction of the ketone, 22' with sodium borohydride. The ketone 22' is prepared as described by Brownridge and Chan (Tetrahedron Letters, 46:4437, 1979). Resolution is carried out on the alcohol, 23' (or 27'), by crystallization of a chiral ester. Thus, 2,5-dimethozytetrahydrofuran, 20', (the appropriate thia or carbon analogs are used as precursors for the synthesis of the thia and carbbicyclo[3.2.1]octanes) is reacted with 1,3-bis (trimethylsiloxy)-1-methoxybuta-1,3-diene, 21', in methylene chloride in the presence of titanium tetrachloride to give 22' in 79% yield. Reduction of the ketone, 22', with sodium borohydride then provides the alcohol as a mixture of stereoisomers, with 23' as a major stereoisomer present and 27' as the minor. The desired syn stereoisomer is separated and the enantiomers are separated by fractional crystallization of chiral esters such as the tartrate ester. The enantiomerically pure alcohol is dehydrated and reesterified with phosphorus exychloride and methanol to provide the anhydromethyl ester, 24', which is reacted with a suitably chosen Grignard reagent (described above) to provide the desired products, (for example, 25').

Synthesis of 2β-Carboxymethyl-3α-diphenylmethoxy [3.2.1]octanes

To prepare the oxa analogs of the 3α-diphenylmethoxytropanes, the synthetic procedure shown in FIG. 6 is followed. The 3α-diphenylmethoxy [3.2.1]octanes are made from the ketone 22'. Either reduction of 22' with sodium borohydride will provide 27' as the minor isomer, or reduction with sodium will provide 27'. As before, 27' is then reacted with a suitably chosen diphenyl diazomethane or dibenzhydrol to provide the desired compounds, 28'.

Synthesis of 2β-Carboxymethyl-3β-diphenylmethoxy [3.2.1]octanes

To prepare the oxa analogs of the 3β-diphenylmethoxytropanes, the synthetic procedure shown in FIG. xx is followed. Compound 23' is prepared and resolved, and purified, and the enantiomerically pure alcohol, 23', is then reacted with a suitably selected diphenyldiazomethane to provide the desired target compounds, 26'.

Reaction of 25', 26' or 28' with suitably chosen lithium reagents will provide the 2β-ketones.

Experimental Details for Synthesis of the 8-oxabicyclo[3.2.1] octanes

Methyl 3-trimethylsiloxybut-2-enoate (1)

A mixture of freshly fused ZnCl2 (1.1 g) and triethylamine (86 mL, 0.62 mol) was stirred for 1 h at room temperature. Methyl acetoacetate (40 mL, 0.37 mol) in benzene (80 mL) was added dropwise, followed by chlorotrimethylsilane (90 mL, 0.72 mol). The mixture was stirred overnight at 40° C. After cooling, ether (500 mL) was added. The mixture was stirred for 1 h and filtered through celite. Volatiles were removed in vacuo. Hexanes (200 mL) were added to the residue which was filtered through celite once again. The filtrate was concentrated to dryness and the residue was distilled through a vigreux column at 79°–82° C. (1.2 mm) to afford 57.6 g (83%) of 1 as a clear oil.

1,3-Bis(trimethylsiloxy)-1-methoxybuta-1,3-diene (2)

To dry diisopropylamine (52 mL, 0.39 mol) in THF (400 mL) at 0° C. under nitrogen was added n-BuLi (146 mL, 2.5M in hexanes, 0.365 mol) followed by TMEDA (48.5 mL, 0.32 mol). The solution was stirred at 0° C. for 30 min then cooled to –78° C. Methyl 3-trimethylsiloxybut-2-enoate, 1, (57.6 g, 0.3 mol) was added to the solution. After stirring for 10 min, chlorotrimethylsilane (61 mL, 0.48 mol) was added. The mixture was allowed to warm up to 0° C. and was then concentrated to dryness on a rotary evaporator at 0° C. (the compound is heat sensitive). Hexanes (dried over molecular sieves; 1 L) were added. The insolubles were removed by filtration and washed with hexanes. The combined filtrate was concentrated to dryness on a rotary evaporator at 0° C. and dried overnight, under high vacuum, at room temperature, to afford 82 g of crude product, 2, which was used in the next step without further purification.

2-Carbomethoxy-8-oxabicyclo[3.2.1] octan-3-one (3)

To 2,5-dimethoxytetrahydrofuran (39.6 g, 0.3 mol) in $CH_2Cl_2$ (anhydrous, 200 mL) at –78° C. under nitrogen was added $TiCl_4$ (66 mL, 0.6 mol). After stirring for 30 min, 1,3-bis(trimethylsiloxy)-1-methoxybuta-1,3-diene, 2, (78 g, 0.3 mol) in $CH_2Cl_2$ (anhydrous, 400 mL) was added at a rate such that the internal temperature was maintained below –55° C. The mixture was stirred for 3 h. Saturated $NaHCO_3$ was added until the mixture was neutral to pH paper. The aqueous layer was extracted with ether (3×1 L). The dried ($MgSO_4$) combined organic layers were concentrated to dryness. The residue was purified by flash chromatography (20% EtOAc/hexanes) to afford 20.5 g (37%) of 3 as a light brown oil.

2-Carbomethoxy-3-{[(trifluoromethyl)sulfonyl]oxy}-8-oxabicyclo[3.2.1]-2-octene (4)

Sodium bistrimethylsilylamide (1.0M solution in THF, 45 mL) was added dropwise to 2-carbomethoxy-8-oxabicyclo[3.2.1] octanone, 3, (7.12 g, 38.65 mmol) in THF (100 mL) at –70° C. under nitrogen. After stirring for 30 min, N-phenyltrifluoromethanesulfonimide (15.19 g, 42.52 mmol) was added as a solid at –7020 C. The reaction was allowed to warm to room temperature and was then stirred overnight. The volatiles were removed on a rotary evaporator. The residue was dissolved in $CH_2Cl_2$ (200 mL) and washed with $H_2O$ (100 mL) and brine (100 mL). The dried ($MgSO_4$) $CH_2Cl_2$ layer was concentrated to dryness. The residue was purified by flash chromatography (10% EtOAc/hexanes) to afford 9.62 g (79%) of 4 as a pale yellow oil.

$^1$H NMR ($CDCL_3$, 100 MHz): δ5.05 (bm, 1H),4.70 (t, 1H), 3.83 (s, 3H), 3.0 (dd, 1H), 2.0–2.35 (m, 5H)

4-Fluorophenyl boronic acid

To a stirred solution of triisopropyl borate (4.6 mL, 20 mmol) in THF (1 mL) at –78° C. under nitrogen was added 4-fluorophenylmagnesium bromide (2M solution in diethylether, 10 mL) dropwise. The mixture was allowed to warm to room temperature. Ether (50 mL) was added, followed by 10% HCl (50 mL). The ether layer was then washed with $H_2O$ (25 mL) and brine (25 mL). The dried ($MgSO_4$) ether layer was concentrated to dryness. The residue was triturated with hexanes to provide an off-white solid which was filtered and dried under vacuum to afford 1.38 g of 4-fluorophenyl boronic acid.

2-Carbomethoxy-3-(4-fluorophenyl)-8-oxabicyclo[3.2.1]-2-octene (5a)

2-Carbomethoxy-3-{[(trifluoromethyl)sulfonyl]oxy}-8-oxabicyclo[3.2.1]-2-octene, 4, (1.87 g, 5.9 mmol), 4-fluorophenyl boronic acid (1.09 g, 7.8 mmol), diethoxymethane (20 mL), LiCl (535 mg, 12.6 mmol), tris(dibenzylideneacetone)dipalladium(0) (230 mg, 0.25 mmol) and $Na_2CO_3$ (2M solution, 5.7 mL) were combined and heated at reflux for 1 h. The mixture was cooled to room temperature, filtered through celite and washed with ether (100 mL). The mixture was basified with $NH_4OH$ and washed with brine. The dried ($MgSO_4$) ether layer was concentrated to dryness. The residue was purified by flash chromatography (10% EtOAc/hexanes) to afford 1.36 g (88%) of 5a as a light brown viscous oil.

$^1$H NMR ($CDCl_3$, 100 MHz): δ6.99–7.12 (m, 4H), 5.00 (bm, 2H), 4.64 (t, 1H), 3.52 (s, 3H), 2.95 (dd, 1H), 1.71–2.19 (m, 5H)

2-Carbomethoxy-3-phenyl-8-oxabicyclo[3.2.1]-2-octene (5b)

Reaction of 2-carbomethoxy-3-{[(trifluoromethyl)sulfonyl]oxy}-8-oxabicyclo[3.2.1]-2-octene, 4, (2.0 g, 6.32 mmol), phenyl boronic acid (1.02 g, 8.36 mmol), diethoxymethane (20 mL), LiCl (578 mg, 13.6 mmol), tris(dibenzylideneacetone)dipalladium(0) (247 mg, 0.25 mmol) and $Na_2CO_3$ (2M solution, 6.1 mL), as described above, gave 1.28 g (82%) of 5b as a light brown viscous oil.

$^1$H NMR ($CDCl_3$, 100 MHz): δ7.1–7.5 (m, 5H), 5.00 (bm, 1H), 4.64 (t, 1H), 3.52 (s, 3H), 2.95 (dd, 1H), 1.71–2.19 (m, 5H)

2-Carbomethoxy-3-(4-chlorophenyl)-8-oxabicyclo[3.2.1]-2-octene (5c)

Reaction of 2-carbomethoxy-3-{[(trifluoromethyl)sulfonyl]oxy}-8-oxabicyclo[3.2.1]-2-octene, 4, (1.0 g, 3.16 mmol), 4-chlorophenyl boronic acid (653 mg, 4.17 mmol), diethoxymethane (10 mL), LiCl (286 mg, 6.75 mmol), tris(dibenzylideneacetone)dipalladium(0) (123 mg, 0.13 mmol) and Na$_2$CO$_3$ (2M solution, 3.0 mL), as described above, gave 0.81 g (92%) of 5c as a light brown viscous oil. $^1$H NMR (CDCl$_3$, 100 MHz): δ7.0–7.35 (q, 4H), 5.00 (bm, 1H), 4.64 (t, 1H), 3.52 (s, 3H), 2.95 (dd, 1H), 1.71–2.19 (m, 5H)

2-Carbomethoxy-3-(3,4-dichlorophenyl)-8-oxabicyclo[3.2.1]-2-octene (5d)

Reaction of 2-carbomethoxy-3-{[(trifluoromethyl)sulfonyl]oxy}-8-oxabicyclo[3.2.1]-2-octene, 4, (1.0 g, 3.16 mmol), 3,4-dichlorophenyl boronic acid (796 mg, 4.17 mmol), diethoxymethane (10 mL), LiCl (286 mg, 6.75 mmol), tris(dibenzylideneacetone)dipalladium(0) (123 mg, 0.13 mmol) and Na$_2$CO$_3$ (2M solution, 3.0 mL), as described above, gave 0.96 g (97%) of 5d as a light brown viscous oil. $^1$H NMR (CDCl$_3$, 100 MHz): 6 6.9–76.5 (m, 4H), 5.00 (bm, 1H), 4.64 (t, 1H), 3.52 (s, 3H), 2.95 (dd, 1H), 1.71–2.19 (m, 5H)

2β-Carbomethoxy-3α-(4-fluorophenyl)-8-oxabicyclo[3.2.1]octane (6a) and 2β-Carbomethoxy-3β-(4-fluorophenyl)-8-oxabicyclo[3.2.1]octane (7a)

To 2-carbomethoxy-3-(4-fluorophenyl)-8-oxabicyclo[3.2.1]-2-octene, 5a, in THF (10 mL) at −70° C. under N$_2$ was added SmI$_2$ (0.1M in THF, 230 mL, 23.0 mmol). After the mixture was stirred for 30 min, MeOH (anhydrous, 25 mL) was added. The mixture was stirred at −70° C. for a further 2 h. The mixture was quenched with TFA (5 mL) and H$_2$O (100 mL). After warming to 0° C., NH$_4$OH was added to attain a pH 11 and the mixture was then stirred for 30 min. The mixture was filtered through celite and washed with ether (400 mL) and then saturated with Na$_2$S$_2$O$_3$. The ether layer was washed with brine. The dried (MgSO$_4$) ether layer was concentrated to dryness. The isomers were separated by gravity column chromatography (10% EtOAc/hexanes) to afford 834 mg (62%) of 6a as a white solid, mp. 58°–60° C. and 300 mg (22%) of 7a as a white solid, mp.118.5°–120.5° C. $^1$H NMR (CDCl$_3$, 400 MHz) (6a): δ6.92–7.17((m, 4H), 4.48 (bd, 2H), 3.58 (s, 3H), 3.20 (dt, 1H), 2.44 (dd, 1H),2.38 (m, 1H), 2.12 (m, 1H), 2.00 (1H), 1.75 (m, 1H),1.63 (m, 1H), 1.32 (ddd, 1H)

$^1$H NMR (CDCl$_3$, 400MHz) (7a): δ6.93–7.20 (m, 4H), 4.65 (m, 2H),3.48 (s, 3H), 3.17 (dt, 1H), 2.78 (d, 1H), 2.73 (dt, 1H), 2.13 (1H), 2.05 (m, 1H), 1.90 (m, 1H), 1.78 (m, 1H), 1.59 (m, 1H)

2β-Carbomethoxy-3α-phenyl-8-oxabicyclo[3.2.1]octane (6b) and 2β-Carbomethoxy-3β-phenyl-8-oxabicyclo[3.2.1]octane (7b)

Reaction of 2-carbomethoxy-3-phenyl-8-oxabicyclo[3.2.1]-2-octene, 5b, (1.17 g, 4.8 mmol) in THF (10 mL) and SmI$_2$ (0.1M in THF, 215 mL, 21.5 mmol), as described above, gave 789 mg (67%) of 6b as a white solid, mp. 96.5°–98° C. and 270 mg (23%) of 7b as a white solid, mp. 102.5°–104° C. $^1$H NMR (CDCl$_3$, 100 MHz) (6b): δ7.25(bs, 5H), 4.51 (bd, 2H), 3.58 (s, 3H), 3.25 (dt, 1H), 2.51 (dd, 1H),2.38 (m, 1H), 1.6–2.2 (m, 4H), 1.41 (ddd, 1H) $^1$H NMR (CDCl$_3$, 100 MHz) (7b): δ7.25 (bs, 5H), 4.65 (m, 2H),3.48 (s, 3H), 3.25 (dt, 1H), 2.78 (d, 1H), 2.73 (dt, 1H), 1.5–2.3 (m, 5H)

2β-Carbomethoxy-3α-(4-chlorophenyl)-8-oxabicyclo[3.2.1]octane (6c) and 2β-Carbomethoxy-3β-(4-chlorophenyl)-8-oxabicyclo[3.2.1]octane (7c)

Reaction of 2-carbomethoxy-3-(4-chlorophenyl)-8-oxabicyclo[3.2.1]-2-octene, 5c, (808 mg, 2.9 mmol) in THF (8 mL) and SmI$_2$ (0.1M in THF, 130 mL, 13.0 mmol), as described above, gave 418 mg (51%) of (6c) as a white solid, mp. 89°–90° C. and 152 mg (19%) of 7c as a white solid, mp. 116°–117° C.

$^1$H NMR (CDCl$_3$, 100 MHz) (6c): δ7.1–7.3(m, 4H), 4.51 (bd, 2H), 3.58 (s, 3H), 3.25 (dt, 1H), 2.51 (dd, 1H),2.38 (m, 1H), 1.6–2.2 (m, 4H), 1.35 (ddd, 1H)

$^{11}$H NMR (CDCl$_3$, 100 MHz) (7c): δ7.1–7.4 (m, 4H), 4.65 (m, 2H),3.48 (s, 3H), 3.20 (dt, 1H), 2.6–2.9(m, 2H), 1.5–2.3 (m, 5H)

2β-Carbomethoxy-3α-(3,4-dichlorophenyl)-8-oxabicyclo[3.2.1]octane (6d) and 2β-Carbomethoxy-3β-(3,4-dichlorophenyl)-8-oxabicyclo[3.2.1]octane (7d)

Reaction of 2-carbomethoxy-3-(3,4-dichlorophenyl)-8-oxabicyclo[3.2.1]-2-octene, 5d, (829 mg, 2.65 mmol) in THF (5 mL) and SmI$_2$ (0.1M in THF, 119 mL, 11.9 mmol), as described above, gave 455 mg (55%) of 6d as a white solid, mp. 88.5°–90° C. and 115 mg (14%) of 7d as a white solid, mp. 132°–133.5° C.

$^1$H NMR (CDCl$_3$, 100 MHz) (6d): δ7.0–7.3 (m, 3H), 4.51 (bd, 2H), 3.61 (s, 3H), 3.25 (dt, 1H), 2.55 (dd, 1H), 1.6–2.4 (m, 5H), 1.35 (ddd, 1H)

$^1$H NMR (CDCl$_3$, 100 MHz) (7d): δ 7.0–7.4 (m, 3H), 4.65 (m, 2H), 3.48 (s, 3H), 3.20 (dt, 1H), 2.6–2.9(m, 2H), 1.5–2.3 (m, 5H)

2-Carbomethoxy-3-camphanate-8-oxabicyclo[3.2.1]oct-2-ene

The ketone, 3 was dissolved in anhydrous THF and cooled to −78° C. under nitrogen. Butyl lithium (1.1 eq.) was added slowly to this cold solution. The resulting solution was allowed to stir for 15 min. The (1S) or (1R) camphanic chloride (1.1 eq.) was added in one portion and the cooling bath was removed. As the solution reached room temperature (ca. 15 min) TLC indicated (30% ethyl acetate in hexane: Rf 0.25) indicated completion of reaction. The reaction was quenched with saturated NaHCO$_3$ and extracted with ether. The layers were separated and the ether further washed with brine. Drying, (MgSO$_4$) filtration and evaporation gave a yellow solid which was purified by flash chromatography (30% ethyl acetate/hexanes) to yield (86%) a white solid, mp. 122°–123.5° C.

The single diastereomers were separated by repeated recrystallization from CH$_2$Cl$_2$/hexanes.

$^1$H NMR (CDCl$_3$, 100 MHz): δ 5.02 (br s, 1H), 4.65 (br t, 1H), 3.72 (s, 3H), 1.6–3.1 (m, 10H), 1.14 (s, 3H), 1.11, 1.13 (2s, 3H), 1.04, 1.06 (2s, 3H).

Hydrolysis of 2-Carbomethoxy-3-camphanate-8-oxabicyclo[3.2.1]oct-2-ene

The camphanate ester was dissolved in a 3:1:1 mixture of THF:H$_2$O:MeOH and LiOH hydrate (1.6 eq.) was added to this in one portion. TLC showed completion of hydrolysis within 1 min. The solution was brought to pH 7 with 1M HCl and organic solvents were evaporated. To the residue was added brine and CH$_2$Cl$_2$ and the layers were separated. The aqueous fraction was extracted with CH$_2$Cl$_2$. Organic extracts were combined and dried (MgSO$_4$), filtered and evaporated. The residue was chromatographed (2% Et$_2$O/CH$_2$Cl$_2$) to give the product in 57% yield.

Compound Characterization

Characterization of the compounds is carried out using standard methods of high field NMR spectra as well as IR, MS and optical rotation. Elemental analysis, TLC and/or HPLC is used as a measure of purity. A purity of >98% is preferred before biological evaluation of these compounds is undertaken. These standards have been easily achieved in prior preparations of CFT itself as well as in the preparation of a number of CFT analogs.

IV. Binding Assays for Candidate Compounds

To evaluate derivatives as to selectivity for the dopamine transporter, compounds are screened in radioreceptor assays using both [$^3$H]CFT and [$^3$H]citalopram as probes for the dopamine and serotonin receptors, respectively. The relative affinities of a compound for either site establishes whether it binds selectively to the dopamine transporter or non-selectively to the serotonin transporter as well. Assays are carried out as follows.

Competition studies to determine the potency of a compound for inhibiting specifically bound [$^3$H]CFT in monkey caudate-putamen membranes are conducted using 0.3–10 nM [$^3$H]CFT and the brain tissue of drug- and disease-free cynomolgus monkeys (*Macaca fascicularis*), which is stored at –85° C. The caudate-putamen is dissected from coronal sections and suspended in 10 vol Tris-HCl (50 mH, pH 7.4 at 4° C.). The tissue is homogenized in a Potter-Elvehjem (glass-teflon) homogenizer with 8 up-and-down strokes using a Tri-R electronic control stirrer motor (2000 rpm approx.). The homogenate is centrifuged twice for 30 min at 38,000×g and resuspended in buffer to yield a final concentration of 4 mg original wet tissue weight/ml of assay buffer. The assay medium contains, in order of addition, buffer (50 mM, Tris-HCl, 120 mM NaCl) or buffer plus test compound (0.2 ml); [$^3$H]CFT (80 Ci/mMol, 0.2 ml, 1 nM); and membrane suspension (0.2 ml) to a final volume of 0.6 ml. Unlabeled (–)-cocaine (30 μM) serves as the baseline drug to detect non-specific binding. Incubation proceeds at 4° C. for 60 min, and the assay is terminated by vacuum filtration over glass fiber filters (Whatman GF/B) pre-soaked with 0.1% bovine serum albumin. The filters are washed with two 5-ml rinses of ice-cold buffer, incubated overnight in fluor (Beckman ready-solve, EP grade), and total radioactivity determined by liquid scintillation spectrometry at 50% counting efficiency. All assays are performed in triplicate, and each experiment is repeated at least twice using tissue from different brains.

To assay binding of the analog to the serotonin transporter, analogs are tested for their ability to compete with labeled [$^3$H]citalopram, a high affinity and selective ligand for serotonin transporter sites (D'Amato et al., J. Pharmacol. Exp. Ther. 242:364–371, 1987). Radioreceptor assays are conducted using tissues prepared as described above. Analogs are incubated with buffer (50 mM Tris HCl; 100 mM NaCl), [$^3$H]citalopram (1 nM), and tissue (1 mg/ml wet tissue weight), incubated 2 h at 4° C., and the incubation terminated by rapid filtration. Non-specific binding is monitored with fluoxetine (1 μM). The sites may first be characterized using other serotonin uptake inhibitors (sertraline, citalopram, fluoxetine, paroxetine, imipramine), other monoamine uptake inhibitors (cocaine, mazindol, GBR 12909, talsupram), and neurotransmitters (dopamine, serotonin, norepinephrine). Subsequently, the potency of CFT or the analog is determined. Parallel studies are conducted with [$^3$H]CFT in order to determine the relative potencies of the analogs at each transporter.

Oxy analogs of potent phenyltropanes were synthesized and their potencies were determined at the dopamine, norepinephrine and serotonin transporters. Several compounds in this series retained the full spectrum of biological activity as the parent nitrogen-containing drugs, particularly high affinity binding to the dopamine, norepinephrine and serotonin transporters in nonhuman primate striatum and to the dopamine transporter in human striatum.

Figure 9:
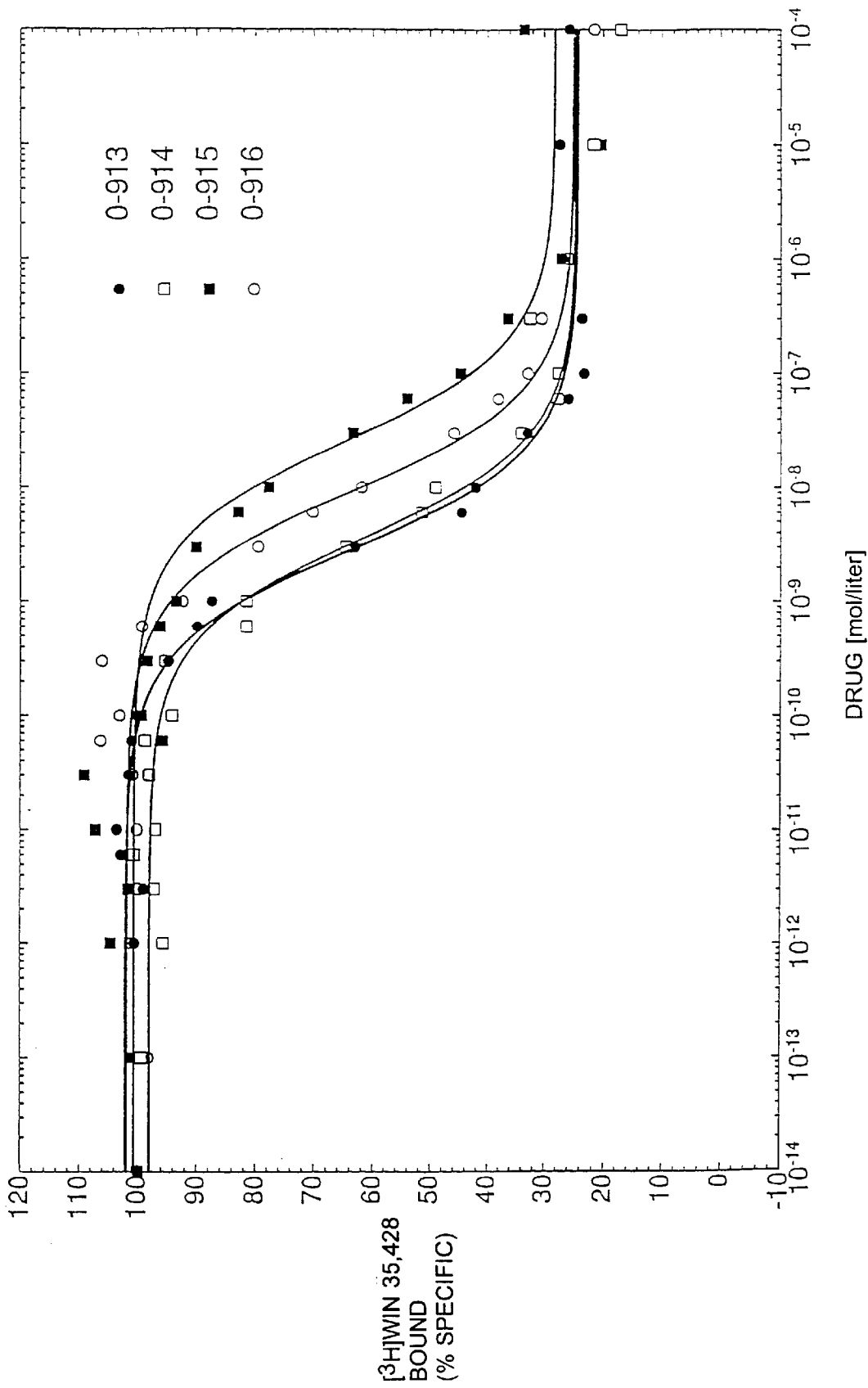
FIGS. 9 and 10 depict the results of competitive binding experiments for four compounds.
Figure 10:
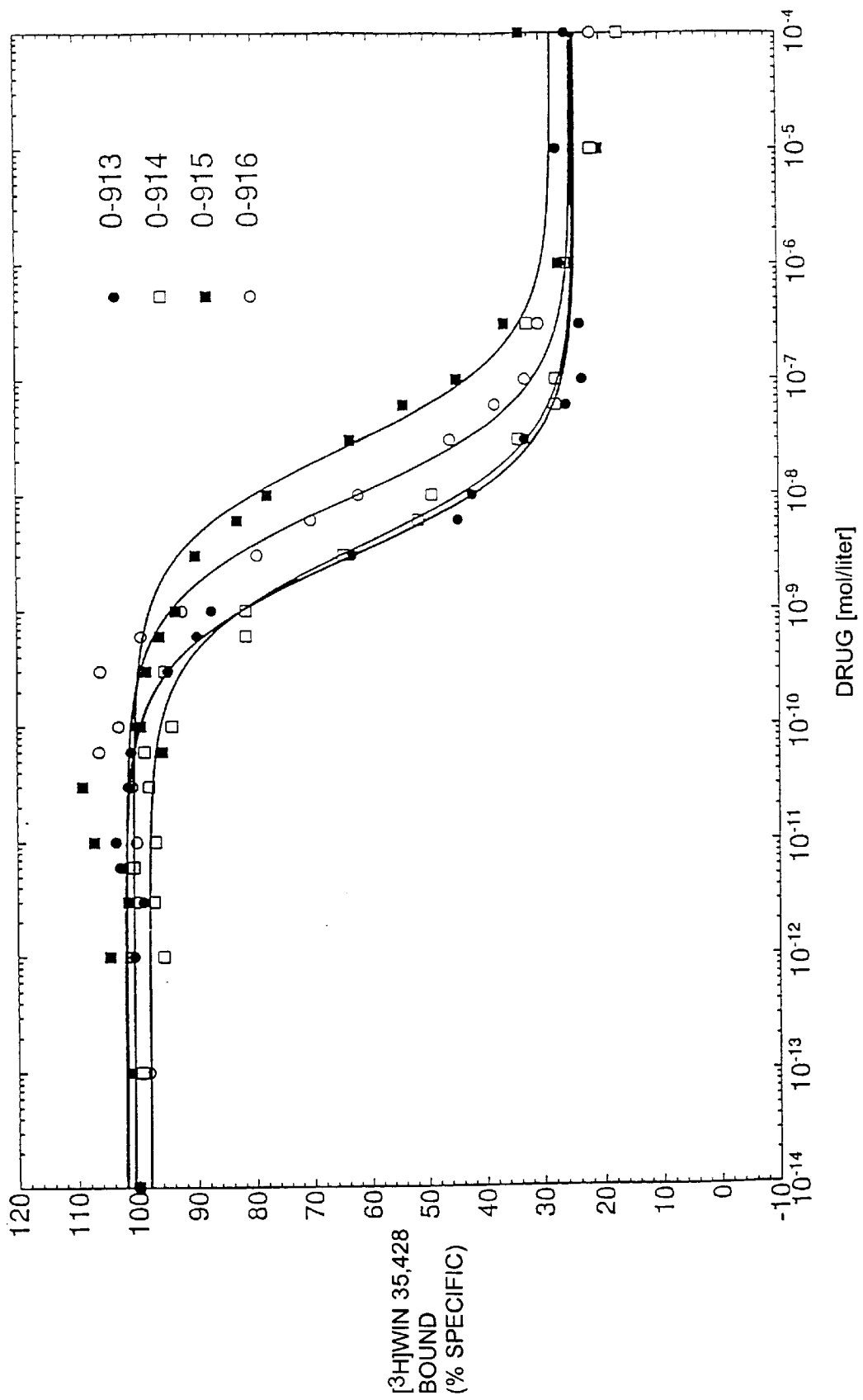

The drugs were assessed in brain tissue of adult cynomolgus monkeys (*Macaca fascicularis*), a species used in our program for brain imaging of the dopamine transporter Madras et al., FASEB J. 2:A1137 (1988), Madras et al., J. Pharmacol. Exp. Ther. 251:131–141, (1989a); Madras et al., Mol. Pharmacol. 36:518–524, (1989b); Madras et al. NIDA Res. Monograph 138:57–69 (1994), Madras et al. *Synapse* 22:239–246 (1996)). Caudate-putamen was the source of the dopamine and serotonin transporters and thalamus was used to assay the norepinephrine transporter. Within this series of non-nitrogen compounds, several exhibited affinities for monoamine transporters in the low nanomolar range. Each of the drugs inhibited radioligand binding to monoamine transporters in a concentration dependent and saturable manner (FIGS. 9 (monkey) and FIG. 10 (human)). Most of the drugs, however, did not fully displace [$^3$H]WIN 35,428 binding to the dopamine transporter, an observation that we have noted in the past for non-phenyltropane drugs (Madras et al., 1989a,b,). The high affinity of tropoxane (0-914) for the dopamine transporter was similar to its affinity for the serotonin transporter and lower for the norepinephrine transporter (Table 1). These values compare favorably with affinities of antidepressant drugs for the norepinephrine and serotonin transporters. They are considerably higher than the affinity of cocaine for the dopamine transporter but within the range of cocaine congeners. The a-epimer of 0914, 0-913, had similar affinity for the dopamine transporter. The halogen substituent on the aromatic ring was critical for high affinity binding as the nonhalogenated compounds bound in the micromolar range. Based on aromatic ring substitutions, the resulting rank order of potency for binding was Cl2>Cl>F>H. The rank order corresponds closely to that observed with the parent nitrogen-containing phenyltropanes, although the effects of halogen substitution on affinity are more pronounced with this series.

In striatum of human post-mortem brain, the drugs bound with similar affinities (Table 2). This series of drugs demonstrates that a nitrogen is not needed for dopamine transporter binding. They furthermore indicate that nitrogen-containing drugs may not be necessary for blockade of the serotonin or norepinephrine transporters. Accordingly, they reveal the possibility of developing a new generation of drugs for the treatment of depression, ADHD, and cocaine abuse. This unique series of compounds indicate new avenues for drug discovery and drug development, significantly modify conventional thinking about transporter-drug interactions, revise structure-activity relationships of the cocaine series, highlight significant differences between the human and monkey dopamine transporter, differences in binding and transport blockade.

Table 1 shows data for binding of novel drugs to the dopamine (A), serotonin (B) and norepinephrine (C) transporters in cynomolgus monkey (*Macaca fascicularis*) brain. Competition studies were conducted with various concentrations of the novel compounds and a fixed concentration of radioligand to label the three monoamine transporters. (A) Inhibition of [$^3$H]WIN 35,428 (1 nM) binding to the dopamine transporter in cynomolgus monkey caudate-putamen. The competition curve for WIN 35,428 is used as a reference standard for each brain preparation; (B) Inhibition of [$^3$H]citalopram (1 nM) binding to the serotonin transporter in monkey caudate-putamen. The competition curve for citalopram is used as a reference standard for each brain preparation; (C) Inhibition of [$^3$H]nisoxetine (0.6 nM) binding to the norepinephrine transporter in monkey thalamus. The competition curve for nisoxetine is used as a reference standard for each brain preparation. Each curve is representative of several experiments, each conducted in triplicate.

TABLE 1

Affinities and monoamine transporter selectivities of tropoxanes in monkey (Macaca fasciculans) brain. The affinity of each compound for the dopamine and serotonin transporter was determined in striatum with [$^3$H]WIN 35,428 and [$^3$H]citalopram, respectively, or the norepinephrine transporter, labeled with [$^3$H]nisoxetine in the thalamus, by radioreceptor assay procedures reported previously (Madras et al., 1996).

| Compound | Dopamine Transporter [$^3$H]WIN 35,428 IC$_{50}$ (nM) | Serotonin Transporter [$^3$H]Citalpram IC$_{50}$ (nM) | Norepineohrine Transporter [$^3$H]Nisoxetine IC$_{50}$ (nM) |
|---|---|---|---|
| O-905 | 1,900 ± 247 | 11,440 ± 447 | |
| O-895 | 546 ± 67 | 2,580 ± 404 | |
| O-913 | 3.06 ± 0.12 | 64.5 ± 10.3 | 62.6 ± 4.7 |
| O-914 | 3.35 ± 0.39 | 6.52 ± 2.05 | 27.0 ± 6.7 |
| O-915 | 34.0 ± 2.4 | 816 ± 79 | |
| O-916 | 9.99 ± 2.26 | 107 ± 17.9 | |

Note that O-895 is compound 25' in FIG. 6, in which R$_1$ is —H and R$_2$ is —F; the 3- substituent is in the β configuration. Compound O-905 is the same as O-895 except that R$_2$ is —F. In each of O-913 through O-916, R$_2$ is —Cl. For O-913 and O-914, R$_1$ is also —Cl, the former having the 3- substituent in the α position, and the latter having that substituent in the β position. For O-915 and O-916, R$_1$ is —H, again, the former having the 3- substituent in the α position, and the latter having that substituent in the β position.

TABLE 2

Affinities of tropoxanes for the dopamine transporter in human putamen. The affinity of each compound for the dopamine transporter, labeled with [$^3$H]WIN 35,428 (1 nM), was measured by radioreceptor assays using standard procedures (Madras et al., 1996), with a striatal tissue concentration of 1 mg/ml.

| Compound | Dopamine Tranporter Affinity [$^3$H]WIN 35,428 OC$_{50}$ (nM) |
|---|---|
| WIN 35,428 | 9.95 ± 1.09 |
| (–)-Cocaine | 57.7 ± 0.8 |
| O-913 (3) | 4.53 ± 1.58 |
| O-914 (2) | 5.01 ± 1.74 |
| O-915 (2) | 28.5 ± 10.8 |
| O-916 (2) | 32.3 ± 0.35 |

Assays

The caudate-putamen was homogenized in 10 volumes (w/v) of ice-cold Tris.HCl buffer (50 mM, pH 7.4 at 4° C.) and centrifuged at 38,700×g for 20 min in the cold. The resulting pellet was suspended in 40 volumes of buffer and the wash procedure was repeated twice. The membrane suspension (25 mg original wet weight of tissue/ml) was diluted in assay buffer to 12 mg/ml for [$^3$H]WIN 35,428 or [$^3$H]citalopram. The affinity of the novel compounds was The dopamine transporter was labeled with [$^3$H]WIN 35,428 ([$^3$H]CFT, 2,B-carbomethoxy-3,B-(4-fluorophenyl)-N-[$^3$H] methyltropane, DuPont-NEN). The affinity of novel compounds for the dopamine transporter was determined in experiments by incubating tissue with a fixed concentration of [$^3$H]WIN 35,428 and a range of concentrations of the compound as previously described (Madras et al., 1989b). The stock solutions were diluted serially in the assay buffer and added (0.2 ml) to the assay medium. The assay tubes received, in Tris.HCl buffer (50 mM, pH 7.4 at 0°–4° C.; NaCl 100 mM), the following constituents at a final assay concentration: drug (0.2 ml; 1 pM–300 yM, depending on affinity), [$^3$H]WIN 35,428 (0.2 ml; 0.3 or 1 nM); membrane preparation (0.2 ml; 1 or 4 mg original wet weight of tissue/ml). The 2 h incubation (0°–4° C.) was initiated by addition of membranes and terminated by rapid filtration over Whatman GF/B glass fiber filters pre-soaked in 0.1% bovine serum albumin (Sigma Chem. Co.). The filters were washed twice with 5 ml Tris.HCl buffer (50 mM), incubated overnight at 0°–4° C. in scintillation fluor (Beckman Ready-Value, 5 ml) and radioactivity (dpm) was measured by liquid scintillation spectrometry (Beckman 1801). Total binding was defined as [$^3$H]WIN 35,428 bound in the presence of ineffective concentrations of the drug. Non-specific binding was defined as [$^3$H]WIN 35,428 bound in the presence of an excess (30 μM) of (–)-cocaine. Specific binding was the difference between the two values.

[$^3$H]Citalopram binding—Serotonin transporter assay

The serotonin transporter was assayed in caudate-putamen membranes using conditions similar to those for the dopamine transporter. The affinity of drugs for the serotonin transporter labeled by [$^3$H]citalopram (spec. act.: 81.86 Ci/mmol, DuPontNEN) was determined by incubating tissue with a fixed concentration of [$^3$H]citalopram and a range of concentrations of the test compounds. The assay tubes received, in Tris-HCl buffer (50 mM, pH 7.4 at 0°–4° C.; NaCl 100 mM), the following constituents at a final assay concentration: drug (0.2 ml of various concentrations); [$^3$H]citalopram (0.2 ml; 1 nM); membrane preparation (0.2 ml; 4 mg original wet weight of tissue/ml). The 2 h incubation (0°–4° C.) was initiated by addition of membranes and terminated by rapid filtration over Whatman GF/B glass fiber filters pre-soaked in 0.1% polyethyleneimine. The filters were washed twice with 5 ml Tris.HCl buffer (50 mM), and the remaining steps were carried out as described above. Total binding was defined as [$^3$H]citalopram bound in the presence of ineffective concentrations of unlabeled citalopram (1 pM) or the test compounds. Non-specific binding was defined as [3H]citalopram bound in the presence of an excess (10 yM) of fluoxetine. Specific binding was the difference between the two values. After conducting preliminary studies with [$^3$H]WIN 35,428 to determine the affinity of altropane for the transporters, [$^{125}$I]altropane was used for subsequent studies.

[$^3$H]Nisoxetine binding: Norepinephrine transporter assay

The norepinephrine transporter was assayed in thalamus membranes using conditions similar to those for the serotonin transporter and adapted from whole rat brain (Gehlert et al., 1995). The affinity of [$^3$H]nisoxetine (spec. act.: 74 Ci/mmol, DuPont-NEN) for the norepinephrine transporter was determined in experiments by incubating tissue with a fixed concentration of [$^3$H] nisoxetine and a range of concentrations of unlabeled nisoxetine. The assay tubes received the following constituents at a final assay concentration: nisoxetine or drug (0.2 ml; 1 pM–300 yM), [$^3$H]nisoxetine (0.2 ml; 0.6 nM); membrane preparation (0.2 ml; 4 mg original wet weight of tissue/ml). The buffer in the assay medium was Tris-HCl: 50 mM, pH 7.4 at 0°–4° C.; NaCl 300 mM. The 16 h incubation at 0°–4° C. was initiated by addition of membranes and terminated by rapid filtration over Whatman GF/B glass fiber filters presoaked in 0.3% polyethyleneimine for 1 hr. The remaining steps are described above. Total binding was defined as [$^3$H] nisoxetine bound in the presence of ineffective concentrations of drug. Non-specific binding was defined as [$^3$H] nisoxetine bound in the presence of an excess (10 yM) of desipramine. Specific binding was the difference between the two values.

V. Behavioral Effects of Candidate Compounds

To the degree possible, candidate compounds for molecular probes should have a full range of cocaine-like biological activity. Candidate compounds found above to have cocaine-like properties in binding studies are assessed further for cocaine-like discriminative stimulus (subjective) effects and their capacity to maintain intravenous self-administration.

For drug discrimination and self administration studies, experiments are conducted with rodents or squirrel monkeys (*Saimiri sciureus*) seated in standard primate chairs enclosed in ventilated, sound-attenuating chambers. The chairs are equipped with response levers, stimulus lights, food pellet dispensers, and pumps for injecting drugs intravenously. Four animals are studied in each experiment, with each subject receiving all drug treatments whenever possible. Response rates and temporal patterns of responding are monitored continuously during daily experimental sessions. Effects of drugs are analyzed in individual subjects by comparing performances during drug sessions with those during control sessions. In experiments involving drug self-administration, i.v. injections of drug solutions (0.2 ml, infused over 200 msec) are scheduled intermittently (as described below). Monkeys in these studies are prepared with indwelling venous catheters according to the general procedures described by Herd et al., (Am. J. Physiol. 27:24–29, 1969). Surgery is conducted in aseptic conditions under halothane/oxygen anesthesia. Catheters are passed by way of a jugular or femoral vein to the level of the right atrium. The distal end of the catheters is passed subcutaneously to a midscapular exit point. Catheters are flushed with 0.9% saline solution and sealed with stainless steel obturators when not in use. Monkeys wear nylon mesh jackets at all times to protect the catheters.

VI. Drug Discrimination

Drug discrimination experiments are conducted using cumulative-dose procedures similar to those described in Madras et al. (Soc. Neurosci. Abst. 16:14, 1990; Pharmacol. Biochem. Behav. 35:949–953, 1990) and Spealman et al. (J. Pharmacol. Exp. Ther. 258:945–953, 1991). Drugs acting in the central nervous system can induce changes in interoceptive states that serve as discriminative stimuli in animals, and there is high pharmacological specificity in the classification of drugs based on their generalized discriminative-stimulus effects. Cumulative-dose procedures have a major advantage over single-dose procedures in that they permit determination of a full dose-effect curve during a single experimental session. Preliminary experiments are first conducted to determine the effective dose ranges and the onsets and durations of action of the drugs. Good agreement has been found between the effects of drugs determined by cumulative-dose procedures and by single-dose procedures when appropriate parameters are selected. Effective doses are studied using single-dose procedures to directly assess the comparability of effects determined by the two techniques.

Drug-discrimination assays are used to characterize the effects of drugs in monkeys trained to discriminate cocaine from vehicle. During experimental sessions, monkeys are seated in chairs equipped with two levers, and a food pellet dispenser mounted between the levers. Each monkey is trained under a 10-response fixed-rate (FR) schedule of food presentation to respond differentially on the left and right levers depending on whether cocaine or vehicle is injected. After i.m. injection of cocaine, 10 consecutive responses on one lever (left for half the monkeys in each group, right for the reminder) will produce food; after i.m. injection of vehicle, 10 consecutive responses on the other lever will produce food. Responses on the inappropriate lever resets the FR requirement. Daily sessions consist of a variable number (n=1–4) of components of the FR schedule. Each component ends after the completion of 10 FRs or after 10 min, whichever occurs first, and each is preceded by an extended timeout period. During most sessions, vehicle is injected during the timeout period preceding the first n-1 components; drug is injected during the timeout period preceding the nth component of the session. During some sessions, however, vehicle is injected during all timeout periods to prevent an invariant association between the fourth component and injection of drug. The number of components per session is varied randomly from day to day. Training continues until a criterion of >90% of responses are made on the injection-appropriate lever. The training dose of cocaine is 0.3–1.0 mg/kg, depending on the performance of individual subjects.

Drug testing begins after criterion-level performances are maintained consistently. Thereafter, test sessions are conducted once per week, always preceded by training sessions with criterion performances. Test sessions consist of four FR components, with each component preceded by an extended timeout period. In each FR component, every tenth response, regardless of lever, produces food. Drugs are studied using the cumulative dosing procedure described previously. Incremental doses are injected i.m. during the timeout periods preceding sequential components of the FR schedule, permitting determination of a four-point dose-effect curve in a single session. In most experiments, five or six different doses of a test drug are studied by determining the effects of overlapping ranges of doses in separate sessions. A test drug is considered to substitute full for cocaine if it engenders >90% of responses on the drug-associated lever.

VII. Drug Self-administration

Self-administration of cocaine and other psychomotor-stimulant drugs is studied under second-order schedules of i.v. drug injection (Bergman et al., J. Pharmacol. Exp. The. 251:150–155, 1989, Spealman et al., Pharmacol. Biochem. Behav. 31:1011–1013, 1991). Under these schedules, high rates of responding can be maintained for extended periods of time by only one or a few injections of drug per session. This feature is particularly useful for comparing drugs with different time courses, which may complicate interpretation of results if injections are scheduled more frequently. Squirrel monkeys are implanted with venous catheters as described previously and trained to respond under a second-order schedule of i.v. cocaine injection similar to the schedule described by Bergman et al. (1989, supra). In the presence of a red light, every 30th response (FR unit) produces a 1-sec change in illumination from red to amber (brief stimulus), and the first FR unit completed after elapse of a 10-min fixed-interval (FI) produces both the brief stimulus and an i.v. injection of cocaine. Following a timeout period, the entire cycle is repeated for a total of ten injections of drug per session.

Initially, responding is maintained using an injection dose of 100 µg/kg cocaine, which usually is optimal for developing i.v. self-administration. After consistent rates and patterns of responding are maintained by cocaine, the effects of a full range of doses of cocaine and of selected candidate drugs is determined. Drugs are studied in different order in different subjects, and experiments with one drug are completed before another drug is studied. Each dose is studied for a block of at least 5 sessions and until no systematic trends in responding are observed for at least 3 consecutive sessions. Blocks of sessions in which vehicle is substituted for drug and responding is extinguished separates experiments with different drugs.

VIII. PET IMAGING

A. PET Imaging Probes

The cocaine analogs described herein provide useful PET imaging probes. PET imaging has at least two applications: to evaluate the time course of accumulation of a candidate cocaine substitute in the brain as well as the duration of receptor occupancy and to monitor cocaine receptors and dopamine nerve terminals in competitor studies (see above).

Cocaine analogs of high affinity are most useful as PET imaging probes because the dose of radioactivity needed to image a target decreases along with decreases in organ dosimetry. In addition, CFT displays a markedly low level of non-specific binding. High affinity analogs are also preferable because dopamine may compete effectively with trace doses of low affinity analogs in vivo, thereby reducing the apparent accumulation in striatum. Affinity of a compound is determined using the in vitro binding assay, and distribution is determined by in vivo and ex vivo receptor autoradiography (described above).

Compounds may also be analyzed for possible in vivo breakdown. Arterial blood samples are withdrawn at predetermined intervals, plasma separated by centrifugation, basified, extracted with $CH_2Cl_2$, the solvent evaporated, and compound metabolites analyzed by HPLC. The percent of water soluble metabolites in the plasma residue is determined by radioactive monitoring and analyzed by HPLC. After appropriate corrections for decay, sensitivity, uniformity and attenuation, the collected image data is reconstructed for tissue concentration maps using a Hanning windowed filtered backprojection. The tissue concentration maps are combined with arterial plasma data to calculate receptor uptake using the model developed by Patlak et al., (Blood Flow Metab. 5:584, 1986). This model relies on the hypotheses (1) that the specific binding of [($^{11}$C]radioligand to striatal membranes can be considered as irreversible for the duration of the PET study; and (2) that non-specific ligand binding is distributed evenly through brain and can be determined from the activity in the cerebellum.

Arterial blood sampling of the monkey will be taken for the same period of time to determine the arterial blood activity curve. The brain distribution, striatum:cerebellar ratio as a function of time and the blood levels of the compound are performed in three monkeys. The following steps are used to evaluate model parameters. 1) Time course of plasma radioactivity is determined. 2) Plasma curves are corrected for metabolism of the tracer and a biexponential function (Gauss-Newton algorithm/non-linear curve-fitting) is fit to the data. 3) From dynamic PET images, time activity curves for striatum, occipital cortex and cerebellum are obtained. 4) The plasma activity of the tracer at the time of PET measurements is determined. 5) The corrected plasma curve at the time of the PET measurements is integrated. 6) The tissue activity ratio (t) [Striatum/Cerebellum]=f [integrated plasma activity (t)/plasma activity (t)] is determined. Initially striatum:cerebellar ratios are calculated as a function of time. The compounds with the highest striatal concentration, fastest blood clearance, least metabolism and least non-specific binding are most preferable in the invention.

Compounds to be used as imaging probes are labelled as follows. This procedure is performed each time before the labeling procedure is done. [$^{11}$C]methyl iodide is prepared as follows: nitrogen gas is bombarded for 15 minutes with 50 µA. The process of converting gaseous COffi to methyl iodide is automated and uses between 1.32–1.5 Ci $^{11}CO_2$. A freshly prepared (under argon) LAH solution is used for the reduction of the $CO_2$. The methyl iodide specific activity is generally 1.32–1.5 Ci. The carboxylic acid ($C_2$) precursor is methylated with [$^{11}$C]methyl iodide in DMF. The mixture is heated at 80° C. for a period of 5 min. The mixture is then flushed with helium or argon into an HPLC system for separation and analysis. The specific activity of the final product should be between 1.–2. Ci/mmol. The column for separation of precursor-product is an Altech C18 prepcolumn. The solvent system is 40% acetonitrile, 60% water and 1% ammonia formate. The extract is evaporated and prepared for i.v. administration.

Prior to PET imaging studies, test animals are subjected to one magnetic resonance imaging (MRI) to determine stereotaxic coordinates of regions of interest using a stereotaxic head holder designed for these studies. The anaesthetized animal (ketamine 10–20 mg/kg/; xylazine 1–2 mg/kg) is placed on the computer controlled imaging table face down. The head is placed into a stereotaxic head holder and the table is moved until the plane of interest is positioned in the imaging field. Two planes of interest are selected, the caudate-putamen and the cerebellum and the selected brain levels are imaged sequentially. Generally, the compound (for example, [$^{11}$C]CFT (400–2,000 Ci/mmol; approximately 1–5 nmoles) is administered to control monkeys and the regional brain distribution association and dissociation rates determined. Following rapid intravenous injection of the compound, dynamic imaging in the selected brain level is started; 30 s scans for 5 min, 1 min scans for next 10 min, 2 min scans for 45 min and 5 min scans thereafter for 30 min. Arterial blood samples of 0.25–0.5 ml for determination of radioactivity and 1.2 ml (*) for determination of lipophilic metabolites by H.P.L.C. are collected according the following time table; 0, 15" 30", 45", 60" (*), 75", 90", 105", 120" (*),5'(*), 10'(*), 15', 20', 30'(*), 45', 60'(*), 75', 90'(*). Plasma and total blood radioactivity are counted in a well counter that is cross calibrated with the tomograph.

PET imaging may be carried but using any appropriate apparatus but is preferably carried out using coded single ring positron tomograph (Brownell et al., Intl. J. Imaging Syst. Tech. 1:207–217, 1989). The analog ring design offers a number of advantages for positron tomography. First, high resolution tomographs can be obtained without sacrificing sensitivity. The analog ring design does not use absorbing masks or intercrystal shielding and is not limited by rejecting photons scattered into adjacent detector elements. Second, high resolution can be obtained without mechanical motion. This results from the use of thin, closely packed detector elements and permits fast dynamic imaging in an easily assembled system (Burnham et al., IEEE Trans. Nucl. Sci. NS 32:889–893, 1991). A single ring analog coded position tomograph (PCR-I) may be used. PCR-I provides adequate resolution (spatial resolution of 4.5 mm) and sensitivity (46 kHz for the slice thickness of 1 cm and activity concentration of 1 µCi/ml) for quantitative biological studies. A moving computer controlled table connected to the camera enables imaging of sequential slices, so images can be acquired in three dimensions. Based on PCR-I, an analog coded cylindrical tomograph, PCR-II, capable of volumetric reconstruction of three-dimensional sources at 3 mm resolution has been designed (Brownell et al., Intl. J. Imaging Syst. Tech. 1:207–217, 1989) and may be used for further analysis.

PET imaging is carried out on conscious human subjects using the techniques outlined above or any other equivalent techniques. SPECT imaging may also be used on human subjects (see, e.g., *Medicine*, Scientific American, Inc., ed. Rubenstein and Federman, 1988; Jaszczak and Coleman, Invest. Radiol. 20:897, 1985; Coleman et al., Invest. Radiol. 21:1, 1986); preferably SPECT imaging employs gamma-imitting derivatives of the analogs described herein (e.g., analogs labelled with $^{123}$I, or $^{99}$Tc).

XI. Analytical Considerations

All target compounds are characterized and their purity analyzed prior to any biological evaluation. High field NMR spectra are measured as well as IR, MS and optical rotation for all test compounds. Elemental analysis, TLC and/or HPLC are used as a measure of purity. A purity of >98% is required before any biological evaluation of these compounds is undertaken.

X. Therapy

The cocaine analogs described herein are useful as cocaine substitutes for treatment of cocaine addiction. The cocaine analogs, may also be useful for the treatment of neurodegenerative diseases, such as Parkinson's disease. For either application, the analogs may be administered, e.g., orally or intravenously in an appropriate dosage, generally 0.01–10 mg/kg.

What is claimed is:

1. A compound of formula:

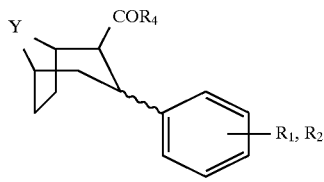

wherein the linkage at each of the 2- and 3-positions independently may be α or β;

wherein Y is C, 0, S, SO; or $SO_2$;

wherein $R_1$ and $R_2$ are each chosen independently from OH, Br, Cl, F, I, $OCH_3$, $CF_3$, $NO_2$, $NH_2$, CN, NCS, OAc, H, or $N_3$; and wherein $R_4$ is $CH_3$, $CH_3CH_2$, $(CH)_2CH$, $CH_3(CH_2)_n$, $(CH_2)_nC_6H_4X$, $C_6H_4X$, $C_6H_5$, $OCH_3$, $OCH(CH_3)_2$, $OC_6H_5$, $OC_6H_4X$, $O(CH_2)_nC_6H_4X$, $O(CH_2)_nCH_3$, or $OCH_3CH_2$, wherein X is Br, Cl, I, F, OH, $OCH_3$, $CF_3$, $NO_2$, $NH_2$, CN, $NHCOCH_3$, $N(CH_3)_2$, $(CH_2)_nCH_3$, $COCH_3$, or $C(CH_3)_3$, wherein n is between 0 and 6 inclusive.

2. The compound of claim 1, wherein $R_4$ is $OCH_3$; and Y is C, O or S; and wherein $R_1$ is H and $R_2$ is F, I, or Cl; or $R_1$ and $R_2$ are both Cl or OH.

3. A compound of formula A), B) or C):

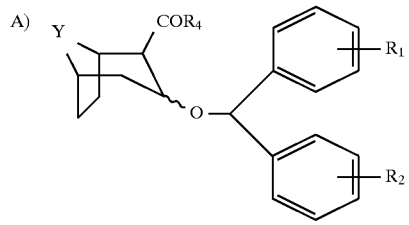

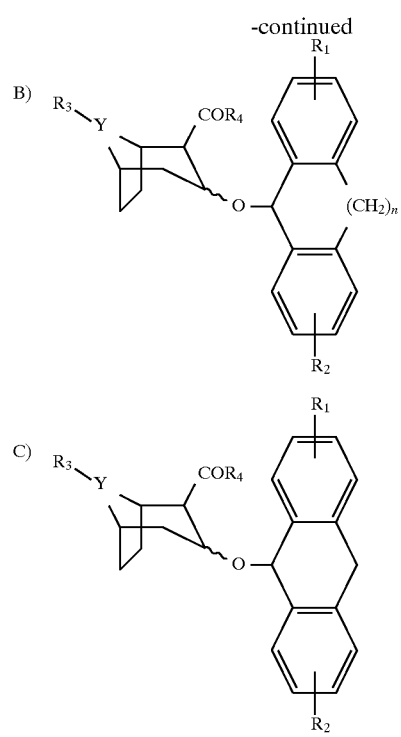

wherein Y is C, O, S, SO, or $SO_2$; and wherein the linkage at each of the 2- and 3-positions independently may be α or β; and wherein $R_1$ and $R_2$ are both 4-F, 4-Cl, 3,4-diCl, 4-I, H, 3,4-diOH, 3,4-diOAc, or 3,4-diOCH$_3$; or $R_1$ is H and $R_2$ is 4-F, 4-Cl, 4-I, 2-F, 2-Cl, 2-I, 3-F, 3-Cl, 3-I, 3,4-diCl, 3,4-diOH, 3,4-diOAc, or 3,4-diOCH,; or $R_1$ is H and $R_2$ is 3-OH-4-Cl, 3-OH-4-F, 3-Cl-4-OH, or 3-F-4-OH; or $R_1$ is the same as $R_2$ and both are chosen from 3-OH-4-Cl, 3-OH-4-F, 3-Cl-4-OH, or 3-F-4-OH; or $R_1$ is not the same as $R_2$ and both are chosen from 3-OH-4-Cl, 3-OH-4-F, 3-Cl-4-OH, or 3-F-4-OH; and wherein $R_4$ is $CH_3$, $CH_3CH_2$, $(CH_3)_2CH$, $CH_3(CH_2)_n$, $(CH_2)_nC_6H_4X$, or $C_6H_4X$, $C_6H_5$, $OCH_3$, $OCH_3CH_2$, $OCH(CH_3)_2$, $OC_6H_5$, $OC_6H_4X$, $O(CH_2)_nC_6H_4X$, or $O(CH_2)_nCH_3$, wherein X is Br, Cl, I, F, OH, $OCH_3$, $CF_3$, $NO_2$, $NH_2$, CN, $NHCOCH_3$, $N(CH_3)_2$, $(CH_2)_n$, $CH_3$, $COCH_3$ or $C(CH_3)_3$, wherein n is between 0 and 6 inclusive.

4. The compound of claim 3, wherein $R_4$ is $OCH_3$; and wherein Y is C; and $R_1$ and $R_2$ are both F or both I; or wherein Y is O; the linkage at the 3-position is α; and each $R_1$ and $R_2$, independently, is Cl, I, or F.

5. The compound of claim 1 in which said compound is labeled with a radioactive or fluorescent label.

6. A therapeutic composition comprising a compound of claim 1, said compound being formulated in a pharmaceutically-acceptable carrier.

7. The compound of claim 1 or claim 2 in which Y is —O—.

8. The compound of claim 1 or claim 2 in which Y is —O— and $R_1$ is —H—.

9. The compound of claim 1 or claim 2 or claim 8 in which Y is —O—, and the C3 substituent is in the a orientation.

10. The compound of claim 9 in which both the C2 and the C3 substituents are in the α orientation.

11. The compound of claim 8 in which $R_2$ is —F or —Cl.
12. The compound of claim 9 in which $R_2$ is —F or
13. The compound of claim 12 in which $R_4$ is —OCH$_3$.
14. A compound having the formula:
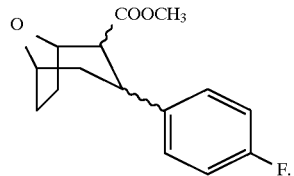
F.
15. A compound having the formula:
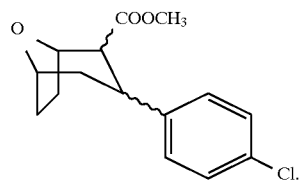
Cl.
* * * * *